United States Patent [19]
Anderson et al.

[11] Patent Number: 5,935,811
[45] Date of Patent: Aug. 10, 1999

[54] NEURON-RESTRICTIVE SILENCER FACTOR NUCLEIC ACIDS

[75] Inventors: David J. Anderson, Altadena; Christopher J. Schoenherr, Pasadena, both of Calif.

[73] Assignee: California Institute of Technology, Pasadena, Calif.

[21] Appl. No.: 08/398,590

[22] Filed: Mar. 3, 1995

[51] Int. Cl.$^6$ .............................. C07H 21/00; C12N 5/10; C12N 15/63; C12P 21/02

[52] U.S. Cl. ...................... 435/69.1; 435/320.1; 435/325; 536/23.1; 536/23.5

[58] Field of Search ................................ 435/69.1, 240.1, 435/320.1, 325; 536/23.5, 23.1

[56] References Cited

FOREIGN PATENT DOCUMENTS

96/29433  9/1996  WIPO.

OTHER PUBLICATIONS

Vandenbergh, D.J., et al., "Chromatin structure as a molecular marker of cell lineage and developmental potential in neural crest–derived chromaffin cells", *Neuron*, 3:507–518, (1989).

Stein, R., et al., "The NGF–Inducible SCG10 mRNA Encodes a Novel Membrane–Bound Protein Present in Growth Cones and Abundant in Developing Neurons", *Neuron*, 1:463–476 (1988).

Wuenschell, C.W., et al., "Analysis of SCG10 Gene Expression in Transgenic Mice Reveals that Neural Specificity Is Achieved through Selective Derepression", *Neuron*, 4:595–602 (1990).

Mori, N., et al., "A Cell Type–Preferred Silencer Element That Controls the Neural–Specific Expression of the SCG10 Gene", *Neuron*, 4:583–594, (1990).

Schoenherr, C.J., et al., "The Neuron–Restrictive Silencer Factor (NRSF): A Coordinate Repressor of Multiple Neuron–Specific Genes", *Science*, 267:1360–1363 (1995).

Maue, R.A., et al., "Neuron–Specific Expression of the Rat Brain Type II Sodium Channel Gene Is Directed by Upstream Regulatory Elements", *Neuron*, 4:233–231 (1990).

Kraner, S.D., et al., "Silencing the Type II Sodium Channel Gene: A Model for Neural–Specific Gene Regulation", *Neuron*, 9:37–44, (1992).

Chong, J.A., et al., "REST: A Mammalian Silencer Protein That Restricts Sodium Channel Gene Expression to Neurons", *Cell*, 80:949–957 (1995).

Mori, N., et al., "A Common Silencer Element in the SCG10 and Type II Na+ Channel Genes Binds a Factor Present in Nonneuronal Cells but Not in Neuronal Cells", *Neuron*, 9:45–54 (1992).

Sauerwald, Angela, et al., "The 5'–Flanking Region of the Synapsin I Gene—A G+C–Rich, TATA–and CAAT–Less, Phylogenetically Conserved Sequence with Cell Type–Specific Promoter Function," *J. Biol. Chem.* 265(25):14932–14937 (Sep. 5, 1990).

Schoenherr, C.J., et al. "Mouse Neural Restrictive Silencer Factor," EMBL, Accession Number: Mm13878 (Jul. 1, 1995).

Krieg, P.A., et al. "Gene Activation in Response to Neural Induction," *Cellular and Molecular Biology Research*, 39:377–383 (1993).

Chowdhury et al., *Nucleic Acids Res.*, vol. 16, pp. 9995–10, 011, 1988.

Reeck et al., *Cell*, vol. 50, p. 667, 1987.

*Primary Examiner*—Anthony C. Caputa
*Assistant Examiner*—Stephen Gucker
*Attorney, Agent, or Firm*—Ivor Elrifi; Mintz, Levin, Cohn, Ferris, Glovsky and Popeo P.C.; John Prince

[57] ABSTRACT

The present invention relates to neuron-restrictive silencer factor proteins, nucleic acids, and antibodies thereto.

7 Claims, 14 Drawing Sheets

Fig. 1A

NRSEs present in neuronal genes

| CONSENSUS: | | TTCAGCACCnCGGAGAGnGCC | | Intragenic Position |
|---|---|---|---|---|
| SOG10 | GCCAT | ------------------- | TCTGC | 5' Regulatory |
| Na CHANNEL | TGGGT | -----A-----C---A--- | AGAGT | 5' Regulatory |
| SYNAPSIN I | CCAGC | ------------------- | TTOGC | 5' Regulatory |
| BDNF | GTCCA | ---------T--------- | AGOGG | 1st Intron |
| GLYCINE RECEPTR (rev) | GGOGT | ---------T--------- | CAGAC | 5' UTR |
| NMDA RECEPTOR | CCCGC | ------------------- | GGCCG | 5' UTR |
| ACH RECPTR B2 | GCGGC | ------------------- | CCACC | 5' UTR |
| NEUROFILIMANE-M | GGGGT | ---------T--------- | GGCCG | 5' Regulatory |
| B-4 TUBLIN | CGCCG | ------------------- | GCCTG | 1st Intron |
| CORT. RELEASING FCTR | GGCGC | ------------------- | CCTCC | 1st Intron |
| CALBINDIN | GCACA | G------------------ | CCCGC | 5' UTR |
| SYNAPTOTAGMIN-4 | GTTCT | ---------------A--- | CGCAG | 5' UTR |
| HES-3 | GGGCA | GG------------------ | AACCC | Coding region |
| SYNAPTOPHYSIN | CGOGC | -C-------T--------- | CGGOG | 1st Intron |

Fig. 1B

Evolutionary conservation of NRSEs

| HUMAN CALBINDIN | | AG---------A------- | | |
|---|---|---|---|---|
| CHICKEN CALBINDIN | | G------------------ | | |
| RAT CALBINDIN | | AG------------------ | | |
| MOUSE CALBINDIN | | AG------------------ | | |
| HUMAN CRF: | | ------------------- | | |
| RAT CRF | | ---------T--------- | | |
| SHEEP CRF | | ------T------------ | | |
| XENOPUS CRF | | ---------------AA-- | | 1st Intron |
| HUMAN NEURONAL NIC ACHR B-2 | | ---------T--------- | | 5' UTR |
| RAT NEURONAL NIC ACHR B-2 | | ---------T--------- | | |
| HUMAN NMDAR (NR1-1) | | ------------------- | | 5' UTR |
| RAT NMDAR (NR1-1) | | --------------AT--- | | |
| HUMAN SYNAPSIN I | | ---T--------------- | | 5' Regulatory |
| RAT SYNAPSIN I | | --T--T------------- | | |

Fig. 1C

NRSEs in non-neuronal genes

```
SOM. ACT. FCTR. (rev)        GTTCT  -----------------A  CGCAG  5' UTR
NCAM                         GCGAT  ---------G-----AA  CCTGG  1st Intron
ATRIAL NATRIURETIC PEPTIDE   TAAAC  -------A------CG-  CGAGG  3' UTR
RAT APRT (rev)               GCTGA  G----G---T------   TGACC  Intron
BOVINE P-450 (rev)           AGTTC  -------G---T----G  AGGGT  Intron
CANINE DISTEMPER VIRUS (rev) TGTCT  ---C-T------G---   AGAGT  Coding region
SHEEP KERATIN                ATGTG  A----------G----   ATGAG  5' Regulatory
MOUSE SKELETAL ACTIN (rev)   GCTTC  GG--------C-----   GCCAG  3' Regulatory
T-CELL RECEPTOR BETA         GTACC  G----A-T--------   TGACA  Coding Region
PIG LACTALBUMIN (rev)        TGTCT  --------G-----T-A  CATTT  Coding Region
```

Fig. 2

Transcriptional Repression by λHZ4

| Reporter Plasmid | pCMV-HZ4 | Percent CAT activity | Fold repression |
|---|---|---|---|
| pCAT3-S36++ | 0 μg | 100 | - |
|  | 1 | 8.3 ± 0.6 | 11.4 |
|  | 4 | 3.1 ± 0.3 | 32 |
| pCAT3 | 0 | 100 | - |
|  | 1 | 77 ± 0.8 | 1.3 |
|  | 4 | 67.5 ± 3.8 | 1.5 |

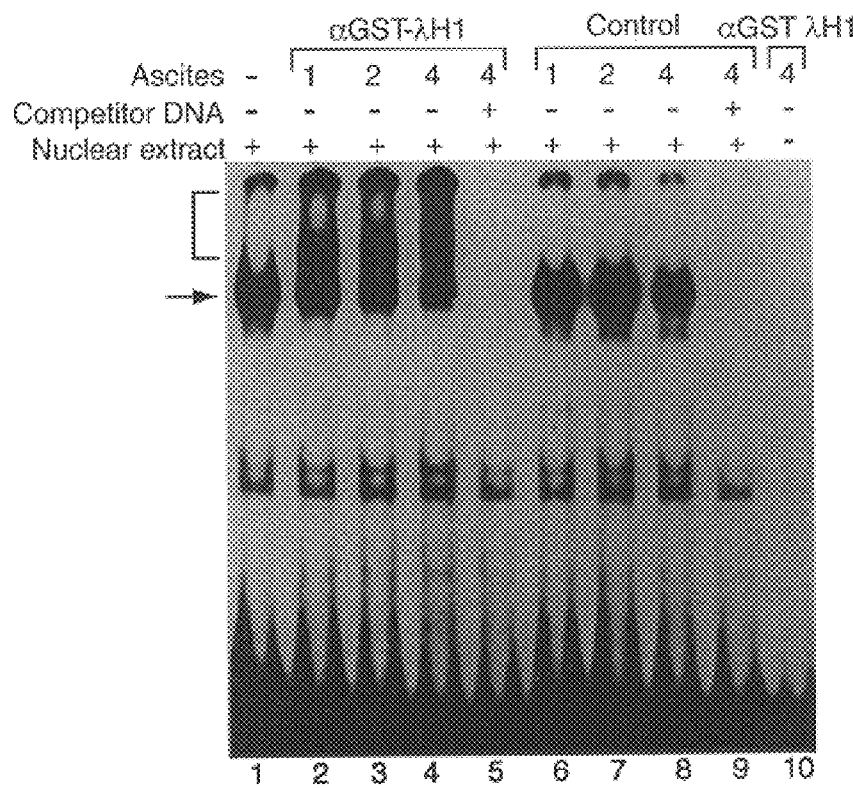
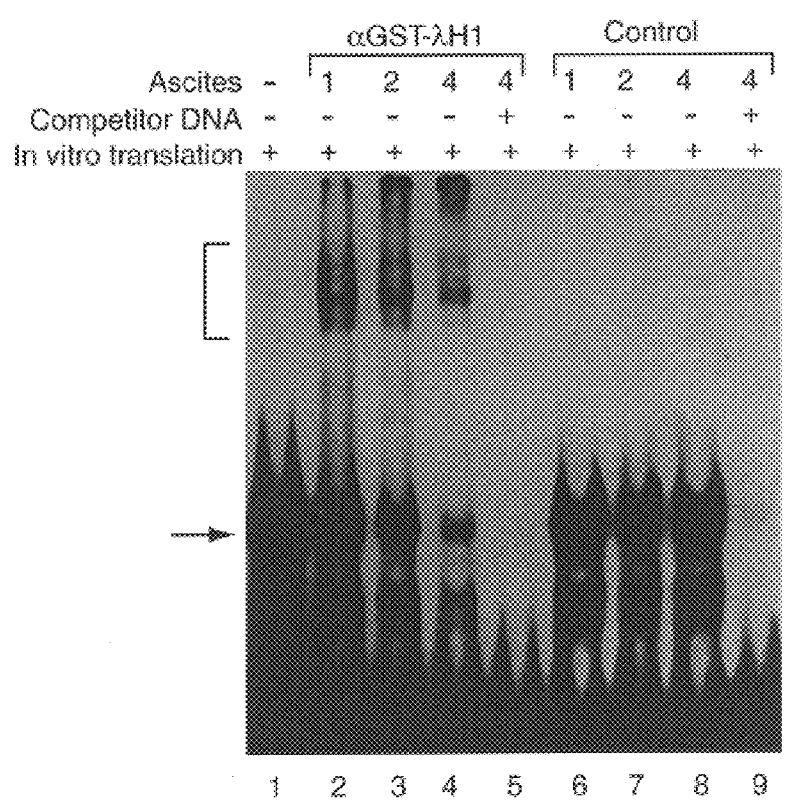
Fig. 4

```
GAATTCC GGG GCC CCA GAC CCT GGC GGC GGC TGC GGC AGC CGA GAC GGC      49
        Gly Ala Pro Asp Pro Gly Gly Gly Cys Gly Ser Arg Asp Gly
         1           5                   10

AGG GCG AGG CCC GGA GGC CTG AGC ACC CTC TGC AGC CCC ACT CCT GGG      97
Arg Ala Arg Pro Gly Gly Leu Ser Thr Leu Cys Ser Pro Thr Pro Gly
 15              20                  25                  30

CCT TCT TGG TCC ACG ACG GCC CCA GCA CCC AAC TTT ACC ACC CTC CCC     145
Pro Ser Trp Ser Thr Thr Ala Pro Ala Pro Asn Phe Thr Thr Leu Pro
                 35                  40                  45

CAC CTC TCC CCC GAA ACT CCA GCA ACA AAG AAA AGT AGT CGG AGA AGG     193
His Leu Ser Pro Glu Thr Pro Ala Thr Lys Lys Ser Ser Arg Arg Arg
             50                  55                  60

AGC GGC GAC TCA GGG TCG CCC GCC CCT CCT CAC CGA GGA AGG CCG AAT     241
Ser Gly Asp Ser Gly Ser Pro Ala Pro Pro His Arg Gly Arg Pro Asn
         65                  70                  75

ACA GTT ATG GCC ACC CAG GTA ATG GGG CAG TCT TCT GGA GGA GGA GGG     289
Thr Val Met Ala Thr Gln Val Met Gly Gln Ser Ser Gly Gly Gly Gly
     80                  85                  90

CTG TTT ACC AGC AGT GGC AAC ATT GGA ATG GCC CTG CCT AAC GAC ATG     337
Leu Phe Thr Ser Ser Gly Asn Ile Gly Met Ala Leu Pro Asn Asp Met
 95                 100                 105                 110

TAT GAC TTG CAT GAC CTT TCC AAA GCT GAA CTG GCC GCA CCT CAG CTT     385
Tyr Asp Leu His Asp Leu Ser Lys Ala Glu Leu Ala Ala Pro Gln Leu
                 115                 120                 125

ATT ATG CTG GCA AAT GTG GCC TTA ACT GGG GAA GTA AAT GGC AGC TGC     433
Ile Met Leu Ala Asn Val Ala Leu Thr Gly Glu Val Asn Gly Ser Cys
             130                 135                 140

TGT GAT TAC CTG GTC GGT GAA GAA AGA CAG ATG GCA GAA CTG ATG CCG     481
Cys Asp Tyr Leu Val Gly Glu Glu Arg Gln Met Ala Glu Leu Met Pro
         145                 150                 155

GTT GGG GAT AAC AAC TTT TCA GAT AGT GAA GAA GGA GAA GGA CTT GAA     529
Val Gly Asp Asn Asn Phe Ser Asp Ser Glu Glu Gly Glu Gly Leu Glu
     160                 165                 170

GAG TCT GCT GAT ATA AAA GGT GAA CCT CAT GGA CTG GAA AAC ATG GAA     577
Glu Ser Ala Asp Ile Lys Gly Glu Pro His Gly Leu Glu Asn Met Glu
175                 180                 185                 190

CTG AGA AGT TTG GAA CTC AGC GTC GTA GAA CCT CAG CCT GTA TTT GAG     625
Leu Arg Ser Leu Glu Leu Ser Val Val Glu Pro Gln Pro Val Phe Glu
                 195                 200                 205

GCA TCA GGT GCT CCA GAT ATT TAC AGT TCA AAT AAA GAT CTT CCC CCT     673
Ala Ser Gly Ala Pro Asp Ile Tyr Ser Ser Asn Lys Asp Leu Pro Pro
             210                 215                 220

GAA ACA CCT GGA GCG GAG GAC AAA GGC AAG AGC TCG AAG ACC AAA CCC     721
Glu Thr Pro Gly Ala Glu Asp Lys Gly Lys Ser Ser Lys Thr Lys Pro
         225                 230                 235
```

Fig. 6A

```
TTT CGC TGT AAG CCA TGC CAA TAT GAA GCA GAA TCT GAA GAA CAG TTT  769
Phe Arg Cys Lys Pro Cys Gln Tyr Glu Ala Glu Ser Glu Glu Gln Phe
    240             245             250

GTG CAT CAC ATC AGA GTT CAC AGT GCT AAG AAA TTT TTT GTG GAA GAG  817
Val His His Ile Arg Val His Ser Ala Lys Lys Phe Phe Val Glu Glu
255             260             265             270

AGT GCA GAG AAG CAG GCA AAA GCC AGG GAA TCT GGC TCT TCC ACT GCA  865
Ser Ala Glu Lys Gln Ala Lys Ala Arg Glu Ser Gly Ser Ser Thr Ala
                275             280             285

GAA GAG GGA GAT TTC TCC AAG GGC CCC ATT CGC TGT GAC CGC TGC GGC  913
Glu Glu Gly Asp Phe Ser Lys Gly Pro Ile Arg Cys Asp Arg Cys Gly
            290             295             300

TAC AAT ACT AAT CGA TAT GAT CAC TAT ACA GCA CAC CTG AAA CAC CAC  961
Tyr Asn Thr Asn Arg Tyr Asp His Tyr Thr Ala His Leu Lys His His
        305             310             315

ACC AGA GCT GGG GAT AAT GAG CGA GTC TAC AAG TGT ATC ATT TGC ACA 1009
Thr Arg Ala Gly Asp Asn Glu Arg Val Tyr Lys Cys Ile Ile Cys Thr
    320             325             330

TAC ACA ACA GTG AGC GAG TAT CAC TGG AGG AAA CAT TTA AGA AAC CAT 1057
Tyr Thr Thr Val Ser Glu Tyr His Trp Arg Lys His Leu Arg Asn His
335             340             345             350

TTT CCA AGG AAA GTA TAC ACA TGT GGA AAA TGC AAC TAT TTT TCA GAC 1105
Phe Pro Arg Lys Val Tyr Thr Cys Gly Lys Cys Asn Tyr Phe Ser Asp
                355             360             365

AGA AAA AAC AAT TAT GTT CAG CAT GTT AGA ACT CAT ACA GGA GAA CGC 1153
Arg Lys Asn Asn Tyr Val Gln His Val Arg Thr His Thr Gly Glu Arg
            370             375             380

CCA TAT AAA TGT GAA CTT TGT CCT TAC TCA AGT CTC AG AAG ACT CAT 1201
Pro Tyr Lys Cys Glu Leu Cys Pro Tyr Ser Ser Ser Gln Lys Thr His
        385             390             395

CTA ACT AGA CAT ATG CGT ACT CAT TCA GGT GAG AAG CCA TTT AAA TGT 1249
Leu Thr Arg His Met Arg Thr His Ser Gly Glu Lys Pro Phe Lys Cys
    400             405             410

GAT CAG TGC AGT TAT GTG GCC TCT AAT CAA CAT GAA GTA ACC CGC CAT 1297
Asp Gln Cys Ser Tyr Val Ala Ser Asn Gln His Glu Val Thr Arg His
415             420             425             430

GCA AGA CAG GTT CAC AAT GGG CCT AAA CCT CTT AAT TGC CCA CAC TGT 1345
Ala Arg Gln Val His Asn Gly Pro Lys Pro Leu Asn Cys Pro His Cys
                435             440             445

GAT TAC AAA ACA GCA GAT AGA AGC AAC TTC AAA AAA CAT GTA GAG CTA 1393
Asp Tyr Lys Thr Ala Asp Arg Ser Asn Phe Lys Lys His Val Glu Leu
            450             455             460
```

Fig. 6B

```
CAT GTG AAC CCA CGG CAG TTC AAT TGC CCT GTA TGT GAC TAT GCA GCT 1441
His Val Asn Pro Arg Gln Phe Asn Cys Pro Val Cys Asp Tyr Ala Ala
        465                 470                 475

TCC AAG AAG TGT AAT CTA CAG TAT CAC TTC AAA TCT AAG CAT CCT ACT 1489
Ser Lys Lys Cys Asn Leu Gln Tyr His Phe Lys Ser Lys His Pro Thr
    480                 485                 490

TGT CCT AAT AAA ACA ATG GAT GTC TCA AAA GTG AAA CTA AAG AAA ACC 1537
Cys Pro Asn Lys Thr Met Asp Val Ser Lys Val Lys Leu Lys Lys Thr
495                 500                 505                 510

AAA AAA CGA GAG GCT GAC TTG CCT GAT AAT ATT ACC AAT GAA AAA ACA 1585
Lys Lys Arg Glu Ala Asp Leu Pro Asp Asn Ile Thr Asn Glu Lys Thr
                515                 520                 525

GAA ATA GAA CAA ACA AAA ATA AAA GGG GAT GTG GCT GGA AAG AAA AAT 1633
Glu Ile Glu Gln Thr Lys Ile Lys Gly Asp Val Ala Gly Lys Lys Asn
                530                 535                 540

GAA AAG TCC GTC AAA GCA GAG AAA AGA GAT GTC TCA AAA GAG AAA AAG 1681
Glu Lys Ser Val Lys Ala Glu Lys Arg Asp Val Ser Lys Glu Lys Lys
            545                 550                 555

CCT TCT AAT AAT GTG TCA GTG ATC CAG GTG ACT ACC AGA ACT CGA AAA 1729
Pro Ser Asn Asn Val Ser Val Ile Gln Val Thr Thr Arg Thr Arg Lys
    560                 565                 570

TCA GTA ACA GAG GTG AAA GAG ATG GAT GTG CAT ACA GGA AGC AAT TCA 1777
Ser Val Thr Glu Val Lys Glu Met Asp Val His Thr Gly Ser Asn Ser
575                 580                 585                 590

GAA AAA TTC AGT AAA ACT AAG AAA AGC AAA AGG AAG CTG GAA GTT GAC 1825
Glu Lys Phe Ser Lys Thr Lys Lys Ser Lys Arg Lys Leu Glu Val Asp
                595                 600                 605

AGC CAT TCT TTA CAT GGT CCT GTG AAT GAT GAG GAA TCT TCA ACA AAA 1873
Ser His Ser Leu His Gly Pro Val Asn Asp Glu Glu Ser Ser Thr Lys
                610                 615                 620

AAG AAA AAG AAG GTA GAA AGC AAA TCC AAA AAT AAT AGT CAG GAA GTG 1921
Lys Lys Lys Lys Val Glu Ser Lys Ser Lys Asn Asn Ser Gln Glu Val
            625                 630                 635

CCA AAG GGT GAC AGC AAA GTG GAG GAG AAT AAA AAG CAA AAT ACT TGC 1969
Pro Lys Gly Asp Ser Lys Val Glu Glu Asn Lys Lys Gln Asn Thr Cys
        640                 645                 650

ATG AAA AAA AGT ACA AAG AAG AAA ACT CTG AAA AAT AAA TCA AGT AAG 2017
Met Lys Lys Ser Thr Lys Lys Lys Thr Leu Lys Asn Lys Ser Ser Lys
655                 660                 665                 670

AAA AGC AGT AAG CCT TCT CGGAATTC                                 2043
Lys Ser Ser Lys Pro Ser
                675
```

Fig. 6C pCAT3-S36++ pCAT3

NEURON-RESTRICTIVE SILENCER FACTOR NUCLEIC ACIDS

FIELD OF THE INVENTION

The present invention relates to neuron-restrictive silencer factor proteins, nucleic acids, and antibodies thereto.

BACKGROUND OF THE INVENTION

The molecular basis of neuronal determination and differentiation in vertebrates is not well understood. It other lineages, systematic promoter analysis of cell-type specific genes has led to the identification of genetically essential transcriptional regulators of lineage determination or differentiation L. M. Corcoran, et al., *Genes and Development* 7, 570–582 (1993); S. Li, et al., *Nature* (London) 347, 528–533 (1990); L. Pevny, et al., *Nature* 349, 257–260 (1991). To apply this approach to the development of neurons, the transcriptional regulation of a neuron-specific gene, SCG10, has been previously examined (D. J. Anderson, R. Axel, *Cell* 42, 649–662 (1985). SCG10 is a 22 Kd, membrane-associated phosphoprotein that accumulates in growth cones and is transiently expressed by all developing neurons (R. Stein, N. Mori, K. Matthews, L.-C. Lo, D. J. Anderson, *Neuron* 1, 463–476 (1988); U. K. Shubart, M. D. Banerjce, *J. Eng. DNA* 8, 389–398 (1989)). Upstream regulatory sequences controlling SCG10 transcription have been analyzed using promoter fusion constructs, both in transient cell transfection assays and in transgenic mice (N. Mori, R. Stein, O. Sigmund, D. J. Anderson, *Neuron* 4, 583–594 (1990); C. W. Wuenschell, N. Mori, D. J. Anderson, *Neuron* 4, 595–602 (1990)). These studies revealed that the 5' flanking region can be functionally separated into two regulatory domains: a promoter-proximal region that is active in many cell lines and tissues, and a distal region that selectively represses this transcription in non-neuronal cells. Deletion of the distal region relieves the repression of SCG10 transgenes in non-neuronal tissues, such as liver, in transgenic mice (C. W. Wuenschell, N. Mori, D. J. Anderson, *Neuron* 4, 595–602 (1990); D. J. Vandenbergh, C. W. Wuenschell, N. Mori, D. J. Anderson, *Neuron* 3, 507–518 (1989)). Furthermore, in transient cell transfection assays this distal region could repress transcription from a heterologous promoter in an orientation- and distance-independent manner (N. Mori, R. Stein, O. Sigmund, D. J. Anderson, *Neuron* 4, 583–594 (1990)), satisfying the criteria for a silencer: a sequence analogous to an enhancer but with an opposite effect on transcription (A. H. Brand, L. Breeden, J. Abraham, R. Sternglanz, K. Nasmyth, *Cell* 41, 41–48 (1985)). The finding that neuron-specific gene expression is controlled primarily by selective silencing stands in contrast to most cell type-specific genes studied previously, in which specificity is achieved by lineage-specific enhancer factors (T. Maniatis, S. Goodbourn, J. A. Fischer, *Science* 236, 1237–1245 (1987); P. Mitchell, R. Tjian, *Science* 245, 371–378 (1989); P. F. Johnson, S. L. McKnight, *Annu. Rev. Biochem.* 58, 799–839 (1989); X. He, M. G. Rosenfeld, *Neuron* 7, 183–196 (1991)).

A detailed analysis of the SCG10 silencer region identified a ca. 24 bp element necessary and sufficient for silencing (N. Mori, S. Schoenherr, D. J. Vandenbergh, D. J Anderson, *Neuron* 9, 1–10 (1992)). Interestingly, similar sequence elements were identified in two other neuron-specific genes: the rat type II sodium (NaII) channel and the human synapsin 1 genes (N. Mori, S. Schoenherr, D. J. Vandenbergh, D. J Anderson, *Neuron* 9, 1–10 (1992); R. A. Maue, S. D. Knaner, R. H. Goodman, G. Mandel, *Neuron* 4, 223–231 (1990); S. D. Kraner, J. A. Chong, H. J. Tsay, G. Mandel, *Neuron* 9, 37–44 (1992); L. Li, T. Suzuki, N. Mori, P. Greengard, *Proceedings of the National Academy of Science (USA)* 90, 1460–1464 (1993)). These sequence elements were shown to possess silencing activity in transfection assays as well, and has been named the neuron-restrictive silencer element (NRSE) (N. Mori, S. Schoenherr, D. J. Vandenbergh, D. J Anderson, *Neuron* 9, 1–10 (1992)); in the context of the NaII channel gene, it has also been called repressor element 1 (RE1) (S. D. Kraner, J. A. Chong, H. J. Tsay, G. Mandel, *Neuron* 9, 37–44 (1992)).

Using electrophoretic mobility shift assays, the NRSEs in the SCG10, NaII channel and synapsin I genes were all shown to form complexes with a protein(s) present in non-neuronal cell extracts, but absent in neuronal cell extracts (Mori et al., supra), Kraner et al., supra, Li et al., supra). This protein was termed the neuron-restrictive silencer factor (NRSF). Both the SCG10 and the NaII channel NRSEs competed with similar efficacy for NRSF, suggesting that this protein could bind both NRSEs (Mori et al., supra). Moreover, mutations in the NRSE that abolished NRSF binding in vitro eliminated the silencing activity of the NRSE in transient transfection assays. These data implicated NRSF in the lineage-specific repression of at least two neuron-specific genes.

SUMMARY OF THE INVENTION

The present invention provides recombinant NRSF proteins, and isolated or recombinant nucleic acids which encode the NRSF proteins.y Also provided are expression vectors which comprise nucleic acid encoding an NRSF protein operably linked to transcriptional and translational regulatory nucleic acid, and host cells which contain the expression vectors.

An additional aspect of the present invention provides methods for producing NRFS proteins which comprise culturing a host cell transformed with an expression vector and causing expression of the nucleic acid encoding the NRSF protein to produce a recombinant NRSF protein.

An additional aspect provides antibodies to the NRSF proteins of the present invention.

BRIEF DESCRIPTION OF THE DRAWINGS

FIGS. 1A (SEQ ID NOS:1–14), 1B (SEQ ID NOS:15–28) and 1C (SEQ ID NOS:29–38) are tables identifying genes containing NRSEs. (A). Neuronal genes that contain NRSE-like sequences (SEQ ID NOS:1–14). The genes listed represent, in order, rat SCG10, rat type II sodium channel, human synapsin I, rat brain-derived neurotrophic factor, human glycine receptor subunit, human NMDA receptor subunit (NR1-1), human neuronal nicotinic acetylcholine receptor β2 subunit, chicken middle molecular weight neurofilament, chicken neuron-specific β4 tubulin, human corticotrophin releasing factor (CRF), chicken calbindin, mouse synaptotagmin-4, rat transcription factor HES-3, rat synaptophysin. Sequences for toad gastrin releasing peptide, rat VGF, and a human olfactory receptor also contained consensus NRSEs but are not shown. (B). Interspecies comparison of NRSE-like sequences (SEQ ID NOS:15–28) in neuronal genes. All homologous sequences are present in similar intragenic positions. Mouse and rat synaptotagmin NRSSEs also show similar conservation (not shown). (C). Non-neuronal genes that contain NRSE-like sequences. The genes listed above represent, in order, rat somatostatin activating factor, the human neural cell adhesion molecule, mouse atrial natriuretic peptide, rate adenine phosphoribosyltransferase, bovine P-450, canine distemper virus L gene, sheep keratin type II, mouse α-skeletal actin, pig gamma-fibrinogen, human T-cell receptor beta subunit, and pig α-lactalbumin. UTR: untranslated region. In parts (A) (SEQ ID NOS:1–14) and (C)(SEQ ID NO:15–28), the genes listed exhibit the top 10 scores in the database search for neuronal and non-neuronal genes, respectively.

FIG. 2 is a table depicting the activity of PC12 cells expressing NRSF. PC12 cells were co-transfected with reporter plasmids and an expression plasmid containing λHZ4. the pCAT3 reporter plasmid consists of the SCG10 proximal region fused to the bacterial CAT enzyme; pCAT3-S36++ consists of pCAT3 with two tandem copies of the S36 NRSE inserted upstream of the SCG10 sequences. The NRSF expression plasmid (pCMV-HZ4) is derived from pCMV-ATG, a modified version of pcDNA3 (Invitrogen) that provides an initiating methionine and a stop codon for the λHZ4 cDNA. To control for non-specific promoter effects, each cotransfection is performed with a constant molar amount of expression plasmid consisting of differing amounts of pCMV-HZ4 and pCMV-ATG. An RSV-LacZ plasmid was included in all transfections to normalize for trasfection efficiency. The activity of each reporter plasmid in the absence of pCMV-HZ4 was normalized to 100% to compare the relative level of repression of each construct. The numbers represent the mean ±SD of two independent experiments performed in duplicate.

FIGS. 4A and 4B showsthat antibodies against GST-λH1 recognize the native NRSF:DNA complex. (A) The indicated amounts (in μl) of αGST-λH1 ascites (48) or a control ascites were added to a mobility shift reaction containing HeLa nuclear extract. The competitor was the S36 oligonucleotide present at 300 fold molar excess. The bracket indicates the supershifted NRSF:DNA complex, and the small arrowhead marks in the NRSF:DNA complex. (B) A mobility shift reaction using a rabbit reticulocyte reaction programmed with λ-H1 encoding RNA. The mobility shift reactions were preformed and analyzed as in the upper panel. For supershift experiments, ascites fluid was included during this incubation. The reactions were performed as in FIG. 3, except that the acrylamide gel used for analysis had an 80:1 acrylamide to bis ratio instead of 30:0.8. The bracket indicates the supershifted λH1-encoded protein: DNA complex, and the large arrowhead marks the λH1-encoded protein:DNA complex. Attempts to obtain an quantitative supershift using higher concentrations of antibody were precluded by the inhibition of DNA biding that occurred when the amount of ascites in the SMSA was increased.

FIG. 4)(data not shown).

FIG. 6 depicts the nucleotide (SEQ ID NO:39) and deduced amino acid sequence (SEQ ID NO:40) of a partial cDNA (λHZ4) for human NRSF (49). The nucleotide sequence is numbered in standard type, and the amino acid sequence in italics. The eight zinc fingers are underlined.

DETAILED DESCRIPTION OF THE INVENTION

Figure 3:
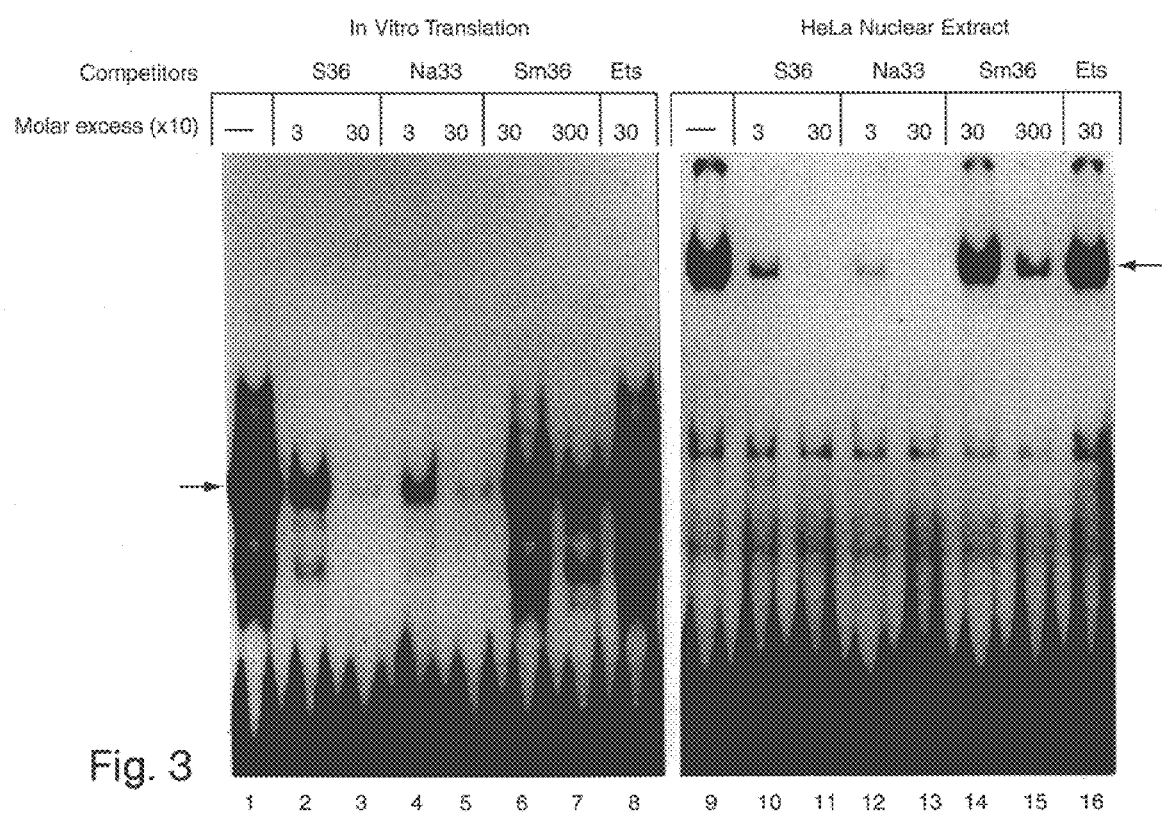
FIG. 3 shows that λH1 encoded NRSF protein has the same sequence specificity of DNA binding as native NRSF. ELectrophoretic mobility shift assays were performed using a HeLa cell nuclear extract or the products of a rabbit reticulocyte lysate in vitro transplation reaction programmed with RNA transcribed from a λH1 fusion construct. The probe was a radiolabeled restriction fragment containing two tandem copies of S36.Competitors used were the S36, Na33 and Sm36 oligonucleotides and an oligonucleotide containing an Ets factor binding site (Ets) (22). The large arrowhead marks the λH1 encoded protein DNA complex (lane 1), the small arrowhead marks the NRSF:DNA complex (lane 9). No complexes were formed by an in vitro translation reaction to which no RNA had been added (data not shown).

The invention provides neuron-restrictive silencer factor (NRSF) nucleic acids and proteins. The NRSF proteins of the invention silence or suppress the expression of neuron-specific genes. Without being bound by theory, it appears that the NRSF protein binds to specific DNA sequences, termed neuron-restrictive silencer elements (NRSE), that function to repress the expression of neuronal genes in non-neuronal cells. Thus, the expression of NRSF prevents a cell from expressing neuronal genes, and thus prevents the cell from becoming a neuron.

The NRSFs of the present invention may be identified in several ways. A NRSF nucleic acid or NRSF protein is initially identified by substantial nucleic acid and/or amino acid sequence homology to the sequences shown in FIG. 6 (SEQ ID NOS:39 and 40). Such homology can be based upon the overall nucleic acid or amino acid sequence.

As used herein, a protein is a "NRSF protein" if it contains a sequence having homology to the amino acid sequences shown in FIG. 6 (SEQ ID NO:40). It is to be understood that the sequence shown in FIG. 6 (SEQ ID NO:40) is a partial sequence of the human NRSF protein, and that both upstream and downstream sequence exists in the full length protein. Accordingly, proteins which contain "overlap" regions with the sequence shown in FIG. 6 (SEQ ID NO:40) are NRSF proteins if the area of overlap has homology to the sequence shown in FIG. 6 (SEQ ID NO:40). Alternatively, NRSF proteins which are contained within the sequence of FIG. 6 (SEQ ID NO:40) will also have homology to FIG. 6 (SEQ ID NO:40). This homology is preferably greater than about 50%, more preferably greater than about 70% and most preferably greater than 85%. In some embodiments the homology will be as high as about 90 to 95 or 98%. This homology will be determined using standard techniques known in the art, such as the Best Fit sequence program described by Devereux et al., Nucl. Acid Res. 12:387–395 (1984). The alignment may include the introduction of gaps in the sequences to be aligned. In addition, for sequences which contain either more or fewer amino acids than the protein shown in FIG. 6 (SEQ ID NO:40), it is understood that the percentage of homology will be determined based on the number of homologous amino acids in relation to the total number of amino acids. Thus, for example, homology of sequences shorter than that shown in FIG. 6 (SEQ ID NO:40), as discussed below, will be determined using the number of amino acids in the shorter sequence.

NRSF proteins of the present invention may be shorter or longer than the amino acid sequence shown in FIG. 6 (SEQ ID NO:40). Thus, in a preferred embodiment, included within the definition of NRSF proteins are portions or fragments of the sequence shown in FIG. 6 (SEQ ID NO:40). In particular, fragments including the "zinc fingers" of the sequence shown in FIG. 6 (SEQ ID NO:40) are preferred. The fragments may range from about 250 to about 600 amino acids. It should be noted that fragments of transcription factors may exhibit all of the functional properties of the intact molecule (H. Weintraub, et al., Science 251, 761–766 (1991); U. Henz, B. Biebel, J. A. Compos-Ortega, Cell 76, 77–88 (1994).

The NRSF proteins and nucleic acids may also be longer than the sequence shown in FIG. 6 (SEQ ID NO:40). Initial experiments suggest that the full length human NRSF protein is in the range of 150 kD, or roughly 1300 amino acids, with the coding region to be roughly 4 kilobases.

In a preferred embodiment, for example when the NRSF protein is to be used to generate antibodies, the NRSF protein must share at least one epitope or determinant with the full length protein, and preferably with the protein shown in FIG. 6 (SEQ ID NO:40). By "epitope" or "determinant" herein is meant a portion of a protein which will generate and bind an antibody. Thus, in most instances, antibodies made to a smaller NRSF protein will be able to bind to a larger portion or the full length protein. In a preferred embodiment, the epitope is unique; that is, antibodies generated to a unique epitope show little or no cross-reactivity with other proteins. The NRSF antibodies of the invention specifically bind to NRSF proteins. By "specifically bind" herein is meant that the antibodies bind to the protein with a binding constant in the range of at least $10^4$–$10^6$ M$^{-1}$, with a preferred range being $10^7$–$10^9$ M$^{-1}$.

In the case of the nucleic acid, the overall homology of the nucleic acid sequence is commensurate with amino acid homology but takes into account the degeneracy in the genetic code and codon bias of different organisms. Accordingly, the nucleic acid sequence homology may be either lower or higher than that of the protein sequence. Similar to the protein sequence, there may be NRSF nucleic acids which contain additional nucleotides as compared to the sequence shown in FIG. 6 (SEQ ID NO:39), and may contain "overlap" regions with the sequence of FIG. 6 (SEQ ID NO:39). NRSF nucleic acids have homology to the FIG. 6 sequence (SEQ ID NO:39) within the overlap region. Thus the homology of the NRSF nucleic acid sequence as directly compared to the nucleic acid sequence of FIG. 6 (SEQ ID NO:39) is preferably greater than 60%, more preferably greater than about 70% and most preferably greater than 80%. In some embodiments the homology will be as high as about 90 to 95 or 98%.

In one embodiment, the nucleic acid homology is determined through hybridization studies. Thus, for example, nucleic acids which hybridize under high stringency to all or part of the nucleic acid sequence shown in FIG. 6 (SEQ ID NO:39) are considered NRSF protein genes. High stringency conditions are generally 0.1×SSC at 37–65° C.

The NRSF proteins and nucleic acids of the present invention are preferably recombinant. As used herein, "nucleic acid" may refer to either DNA or RNA, or molecules which contain both deoxy- and ribonucleotides. The nucleic acids include genomic DNA, cDNA and oligonucleotides including sense and anti-sense nucleic acids. Such nucleic acids may also contain modifications in the ribose-phosphate backbone to increase stability and half life of such molecules in physiological environments.

Specifically included within the definition of nucleic acid are anti-sense nucleic acids. Generally, anti-sense nucleic acids function to prevent expression of mRNA, such that a NRSF protein is not made. An anti-sense nucleic acid hybridizes to the nucleic acid sequence shown in FIG. 6 (SEQ ID NO:39) or its complement, but may contain ribonucleotides as well as deoxyribonucleotides. It is to be understood that the anti-sense nucleic acid may be shorter than the full-length gene; that is, the anti-sense nucleic acid need only hybridize to a portion of the complement of the NRSF gene to suppress expression of the NRSF. Preferably, hybridization of the anti-sense nucleic acid to the endogeneous NRSF mRNA forms a stable duplex which prevents the translation of the mRNA and thus the formation of functional NRSF protein. Accordingly, preferably hybridization of the anti-sense nucleic acid prevents initiation of translation, or results in premature termination of translation such that a functional protein or peptide is not made. Alternatively, the anti-sense nucleic acid binds to the complement of the portion of the gene which confers functionality, i.e. DNA binding. The hybridization conditions used for the determination of anti-sense hybridization will generally be high stringency conditions, such as 0.1× SSC at 65° C.

The nucleic acid may be double stranded, single stranded, or contain portions of both double stranded or single stranded sequence. By the term "recombinant nucleic acid" herein is meant nucleic acid, originally formed in vitro, in general, by the manipulation of nucleic acid by endonucleases, in a form not normally found in nature. Thus an isolated NRSF nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it can replicate non-recombinantly, i.e. using the in vivo cellular machinery of the host cell rather than in vitro manipulations; however, such nucleic acids, once produced recombinantly, although subsequently replicated nonrecombinantly, are still considered recombinant for the purposes of the invention.

Similarly, a "recombinant protein" is a protein made using recombinant techniques, i.e. through the expression of a recombinant nucleic acid as depicted above. A recombinant protein is distinguished from naturally occurring protein by at least one or more characteristics. For example, the protein may be isolated away from some or all of the proteins and compounds with which it is normally associated in its wild type host. The definition includes the production of a NRSF protein from one organism in a different organism or host cell. Alternatively, the protein may be made at a significantly higher concentration than is normally seen, through the use of a inducible promoter or high expression promoter, such that the protein is made at increased concentration levels. Optionally, the protein may be made in a cell type which usually does not express the NRSF protein, or at a stage in development which is different from the normal or wild-type time of expression. Alternatively, the protein may be in a form not normally found in nature, as in the addition of an epitope tag or amino acid substitutions, insertions and/or deletions. Although not usually considered recombinant, the definition also includes proteins made synthetically.

Also included with the definition of NRSF protein are NRSF proteins from other organisms, which are cloned and expressed as outlined below. In a preferred embodiment, the NRSF proteins are from humans, although NRSF proteins from rats, mice, Xenopus, drosophila, zebrafish and *C. elegans* are also included within the definition of NRSF proteins. It should be noted that the homology of NRSF nucleic acids from different organisms is quite high as demonstrated with Southern blot analysis of the human, mouse and rat genes. The human sequence was used to clone mouse and Xenopus NRSF nucleic acids.

An NRSF protein may also be defined functionally. A NRSF is capable of binding to at least one NRSE, or a consensus NRSE, such as depicted in FIG. 1. By "binding to a NRSE" herein is meant that the NRSF can cause a shift in the electrophoretic molibity of the NRSE in an electrophoretic mobility shift assay as outlined below. It is to be understood that the full length protein is not required for binding to a NRSE, since the partial sequence shown in FIG. 6 (SEQ ID NO:40) is sufficient for binding to an NRSE.

Alternatively, an NRSF may be defined as a protein which is capable of suppressing or silencing the expression of neuronal genes. By "neuronal genes" herein is meant genes which are preferentially expressed in neurons. Preferably, the neuronal gene is not expressed significantly, if at all, in any other types of tissues. Examples of neuronal genes include, but are not limited to, SCG10, NaII channel, synapsin I, brain-derived neurotrophic factor, glycine receptor subunit, N-methyl-D-aspartate receptor, neuronal nicotinic acetylcholine receptor β2 subunit, middle molecular weight neurofilament, neuron-specific β4 tubulin, corticotrophin releasing factor (CRF), calbindin, synaptotagmin-4, transcription factor HES-3, and synaptophysin.

Also included within the definition of a NRSF are amino acid sequence variants. These variants fall into one or more of three classes: substitutional, insertional or deletional variants. These variants ordinarily are prepared by site specific mutagenesis of nucleotides in the DNA encoding the NRSF protein, using cassette mutagenesis or other techniques well known in the art, to produce DNA encoding the variant, and thereafter expressing the DNA in recombinant cell culture as outlined above. However, just as for wild-type NRSF proteins, variant NRSF protein fragments having up to about 100–150 residues may be prepared by in vitro synthesis using established techniques. Amino acid sequence variants are characterized by the predetermined nature of the variation, a feature that sets them apart from naturally occurring allelic or interspecies variation of the NRSF protein amino acid sequence. The variants typically exhibit the same qualitative biological activity as the naturally occurring analogue, although variants can also be selected which have modified characteristics.

While the site or region for introducing an amino acid sequence variation is predetermined, the mutation per se need not be predetermined. For example, in order to optimize the performance of a mutation at a given site, random mutagenesis may be conducted at the target codon or region and the expressed NRSF protein variants screened for the optimal combination of desired activity. Techniques for making substitution mutations at predetermined sites in DNA having a known sequence are well known, for example, M13 primer mutagenesis. Screening of the mutants is done using assays of NRSF activities; for example, mutated NRSF proteins may be tested for binding to NRSEs.

Amino acid substitutions are typically of single residues; insertions usually will be on the order of from about 1 to 20 amino acids, although considerably larger insertions may be tolerated. Deletions range from about 1 to 30 residues, although in some cases deletions may be much larger; for example, biological activity is present with the partial sequence depicted in FIG. 6 (SEQ ID NO:40).

Substitutions, deletions, insertions or any combination thereof may be used to arrive at a final derivative. Generally these changes are done on a few amino acids to minimize the alteration of the molecule. However, larger changes may be tolerated in certain circumstances.

The NRSF protein may also be made as a fusion protein, using techniques well known in the art. Thus, for example, for the creation of monoclonal antibodies, if the desired epitope is small, the NRSF protein may be fused to a carrier protein to form an immunogen. Alternatively, the NRSF protein may be made as a fusion protein to increase expression.

Once the NRSF nucleic acid is identified, it can be cloned and, if necessary, its constituent parts recombined to form the entire NRSF nucleic acid. For example, all or part of the nucleic acid depicted in FIG. 6 (SEQ ID NO:39) may be used to clone the full length NRSF nucleic acid from either a cDNA library or from the genome of an organism. This is done using techniques well known in the art. For example, by sequencing overlapping clones both upstream and downstream to the sequence shown in FIG. 6 (SEQ ID NO:39), the entire cDNA sequence may be elucidated. As outlined above, it appears that the full length cDNA is roughly 4 kilobases long, of which roughly 2 kilobases is shown in FIG. 6 (SEQ ID NO:39). Once isolated from its natural source, e.g., contained within a plasmid or other vector or excised therefrom as a linear nucleic acid segment, the recombinant NRSF nucleic acid can be further used as a probe to identify and isolate other NRSF nucleic acids from other organisms. It can also be used as a "precursor" nucleic acid to make modified or variant NRSF nucleic acids and proteins.

Using the nucleic acids of the present invention which encode NRSF, a variety of expression vectors are made. The expression vectors may be either self-replicating extrachromosomal vectors or vectors which integrate into a host genome. Generally, these expression vectors include transcriptional and translational regulatory nucleic acid operably linked to the nucleic acid encoding the NRSF protein. "Operably linked" in this context means that the transcriptional and translational regulatory nucleic acid is positioned relative to the coding sequence of the NRSF protein in such a manner that transcription is initiated. Generally, this will mean that the promoter and transcriptional initiation or start sequences are positioned 5' to the NRSF coding region. The transcriptional and translational regulatory nucleic acid will generally be appropriate to the host cell used to express the NRSF protein; for example, transcriptional and translational regulatory nucleic acid sequences from Bacillus are preferably used to express the NRSF protein in Bacillus. Numerous types of appropriate expression vectors, and suitable regulatory sequences are known in the art for a variety of host cells.

In general, the transcriptional and translational regulatory sequences may include, but are not limited to, promoter sequences, ribosomal binding sites, transcriptional start and stop sequences, translational start and stop sequences, and enhancer or activator sequences. In a preferred embodiment, the regulatory sequences include a promoter and transcriptional start and stop sequences.

Promoter sequences encode either constitutive or inducible promoters. The promoters may be either naturally occurring promoters or hybrid promoters. Hybrid promoters, which combine elements of more than one promoter, are also known in the art, and are useful in the present invention.

In addition, the expression vector may comprise additional elements. For example, the expression vector may have two replication systems, thus allowing it to be maintained in two organisms, for example in mammalian or insect cells for expression and in a procaryotic host for cloning and amplification. Furthermore, for integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

In addition, in a preferred embodiment, the expression vector contains a selectable marker gene to allow the selection of transformed host cells. Selection genes are well known in the art and will vary with the host cell used.

The NRSF proteins of the present invention are produced by culturing a host cell transformed with an expression vector containing nucleic acid encoding a NRSF protein, under the appropriate conditions to induce or cause expression of the NRSF protein. The conditions appropriate for NRSF protein expression will vary with the choice of the expression vector and the host cell, and will be easily ascertained by one skilled in the art through routine experimentation. For example, the use of constitutive promoters in the expression vector will require optimizing the growth and proliferation of the host cell, while the use of an inducible promoter requires the appropriate growth conditions for induction. In addition, in some embodiments, the timing of the harvest is important. For example, the baculoviral systems used in insect cell expression are lytic viruses, and thus harvest time selection can be crucial for product yield.

Appropriate host cells include yeast, bacteria, archebacteria, fungi, and insect and animal cells, including mammalian cells. Of particular interest are *Drosophila melangaster* cells, *Saccharomyces cerevisiae* and other yeasts, *E. coli, Bacillus subtilis*, SF9 cells, C129 cells, 293 cells, Neurospora, BHK, CHO, COS, and HeLa cells, immortalized mammalian myeloid and lymphoid cell lines.

In one embodiment, the NRSF nucleic acids, proteins and antibodies of the invention are labelled. By "labelled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the compound at any position.

The NRSF proteins and nucleic acids encoding NRSF proteins find use in a number of applications. All or part of the NRSF nucleic acid sequence depicted in FIG. 6 (SEQ ID NO:39) may be used to clone longer NRSF sequences, preferably including the initiation and stop codons, and more preferably including any upstream regulatory sequences as well. The NRSF proteins may be coupled, using standard technology, to affinity chromatography columns, for example to purify NRSF antibodies.

In particular, nucleic acids encoding NRSF proteins may be used to disrupt the expression of NRSF proteins within a cell, to allow the cell to express neuronal proteins. For example, NRSF genes containing deletions of significant coding portions may be inserted into the genome of the host, using an integration expression vector and homologous recombination, to disrupt the expression of NRSF protein, thus allowing the expression of neuronal genes. For example, the expression of NRSF in neuronal precursor cells may be eliminated, thus allowing the precursor cells to differentiate into neurons. For example, precursor cells may be removed from a patient, treated with NRSF nucleic acid to suppress the expression of NRSF and thus allow expression of neuronal genes and differentiation into neurons, and then the neurons transplanted back into the patient as needed.

Similarly, anti-sense nucleic acids may be introduced into precursor cells for the same purpose. The anti-sense nucleic acid binds to the mRNA encoding the NRSF and prevent translation, thus reducing or eliminating the NRSF within the cell and allowing differentiation into neurons.

The NRSF proteins may also be used as targets to screen for drugs that inhibit the activity of the NRSF protein, for example in commercial drug development programs. These inhibitory drugs may be used as outlined above to allow differentiation into neurons. NRSF proteins are also useful to search for additional neuronal genes. For example, putative neuronal genes may be combined with NRSF protein and assayed for binding, for example using a mobility shift assay as described herein. Binding of NRSF to a regulatory portion of a gene indicates a strong possibility of the gene being a neuronal gene.

The NRSF proteins are also useful to make antibodies as well. Both polyclonal and monoclonal antibodies may be made, with monoclonal antibodies being preferred. This is done using techniques well known in the art. The antibodies may be generated to all or part of the NRSF sequence. The antibodies are useful to purify the NRSF proteins of the present invention.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference.

EXAMPLES

Example 1

Isolation of a cDNA Clone Encoding NRSF

In previous work, NRSF binding activity was detected in nuclear extracts from non-neuronal cell lines, such as HeLa cells, but not in neuronal cell lines such as PC12 cells (15) N. Mori, S. Schoenherr, D. J. Vandenbergh, D. J Anderson, *Neuron* 9, 1–10 (1992). Therefore, to isolate a cDNA clone encoding NRSF, a HeLa cell λgt11 cDNA expression library (the generous gift of Paula Henthorn) was screened according to methods of situ detection of filter-bound DNA-binding proteins [H. Singh, J. H. LeBowitz, A. S. Baldwin, Jr., P. A. Sharp, *Cell* 52, 415 (1988); C. R. Vinson, K. L. LaMarco, P. F. Johnson, W. H. Landschulz, S. L. McKnight, *Genes & Dev.* 2, 801 (1988)]. Briefly, the nitrocellulose filters which overlaid the phage plaques were treated with guanidine-HCl and probed as in Vinson et al. (1988) and washed as in Singh et al. (1988). The probe was generated by restriction digest with EcoRI and XhoI of a plasmid containing three Na33 oligonucleotides inserted into the HindIII site of pBluescript and was labeled using [α-$^{32}$P] dATP and dTTP and Klenow fragment. The correct fragment was isolated by PAGE and was further purified using Elutip chromatography (Schleicher and SCHuc11). Probes containing two copies of the S36 or Sm36 were isolated in the same manner and were used to confirm the DNA-binding specificity of plaques that recognized the Na33 probe. To obtain additional cDNAs, a HeLa cell λZAPII (Stratagene) and a Balbc/3T3 cell EXlog (the generous gift of S. Tactigian and B. Wold) cDNA library were screened using standard hybridization procedures. The nucleotide sequence of both strands of each cDNA was determined by the dideoxy sequencing method using Sequenase version 2.0 (U.S. Biochemicals). The resulting sequences were assembled and analyzed using the GCG [J. D. Devereux, P. Haeberli, O. Smithies, *Nuc. Acids. Res.* 12, 387 (1984)] and BLAST programs [S. F. Altschul, W. Gish, W. Miller, E. W. Myers, D. j. Lipman, *J. Mol. Biol.* 215, 403 (1990)]. The PROSITE data base [A. Bairoch, *Nuc. Acids Res.* 20, 2013 (1992)] was used to search for protein sequence motifs. cDNAs for mouse NRSF were isolated from the Balbc/3T3 library to permit analysis of the expression pattern of NRSF mRNA in the mouse and the rat. The longest cDNA, λM5 shows 81% amino acid sequence identity with the human sequence over the entire clone, and the identity over the zinc finger domain (including the interfinger sequence) is 96% (241/252)(data not shown).

Approximately two million plaques were screened initially using a radiolabeled probe consisting of three tandemly arrayed copies of the NaII NRSE, Na33. The DNA probes for screening the library are referred to as S36, Sm36 and Na33. S36 and Na33 are the NRSE elements present in the SCG10 and NaII channel genes, respectively. Both of these elements have previously been shown to be sufficient to confer silencing activity and are bound by NRSF. The Sm36 sequence contains two point mutations in the S36 sequence and has an approximately 100 fold lower affinity for NRSF.

The sequence of the top strand of the oligonucleotides used for library screening and EMSAs are given below. The upper case sequences represent actual genomic sequence, the lower case sequences are used for cloning purposes.

S36: agctGCAAAGCCATTTCAGCACCACG-GAGAGTGCCTCTGC (SEQ ID NO:49);

Na33: ageATTGGGTTTCAGAACCACGGACAG-CACCAGAGTa; (SEQ ID NO:50)

Syn: agettATGCCAGCTTCAGCACCGCGGA-CAGTGCCTTCCa; (SEQ ID NO:51)

BDNF: agettAGAGTCCATTCAGCACCTTGGA-CAGAGCCAGCGGa; (SEQ ID NO:52)

Ets: agettGCGGAACGGAAGCGGAAACCGa (SEQ ID NO:53).

Positive plaques from this screen were tested further for sequence specific DNA-binding by an additional screen with probes containing the SCG10 NRSE S36 or the mutated NRSE, Sm36 (15) N. Mori, S. Schoenherr, D. J. Vandenbergh, D. J Anderson, *Neuron* 9, 1–10 (1992). One phage was identified, λH1, that like native NRSF bound both the S36 and the Na33 probes but not the control Sm36 probe.

As an additional test of the authenticity of the cDNA clone, the DNA-binding specificity of its encoded protein was compared to that of native NRSF present in HeLa cell nuclear extracts using an electrophoretic mobility shift assay (EMSA). To generate recombinant protein, the λH1 insert was subcloned into the EcoRI site of pRSET B (Invitrogen), which provided an in-fromae start codon, a poly-histidine tag, and a T7 promoter, Recombinant λH1 was produced by in vitro transcription from linearized plasmid and in vitro translation using a rabbit reticulocyte lysate according to manufacturer's protocol (Promega). Mobility shift assays were performed as described except 0.5 μg supercoiled plasmid and 10 μg of BSA were included in each reaction. This mixture was incubated for 10 minutes on ice. Labeled probe (0.3 ng) in then added to the reaction, followed by a 10 minute incubation at room temperature. Probes were labeled and isolated as described above, and unlabeled competitors were single copy, double-strand oligonucleotides added at the indicated molar excess. Electrophoresis was performed on a 4% polyacrylamide gel (30:0.8% acrylamide:bis) in 0.25×TBE and electrophoresed for 2 hr at 10 V/cm at room temperature.

The results indicated that both proteins form complexes with the S36 probe (FIG. 3, lane 1, large arrowhead to left of panel vs. lane 9, small arrowhead to right of panel). The faster mobility of the λH1-encoded protein:DNA complex most likely reflects a difference in molecular weight between the fusion protein and the endogenous factor, as the λH1 cDNA does not encode the full-length protein (see below). The sequence specificity of those complexes was tested by competition experiments using unlabeled, double-stranded oligonucleotide binding sites. The SCG10 (S36) and the NaII channel genes (Na33) NRSEs showed similar ability to compete both the λH1-encoded and the native protein:DNA complexes (FIG. 3, compare lanes 2–5 and 10–13). These complexes, however, were poorly competed by the mutated NRSE (Sm36, lanes 6, 7 and 14, 15), and no competition was seen with a control oligonucleotide containing an Ets factor binding site (lanes 8 and 16) (22) K. Lamarco, C. C. Thompson, B. P. Byers, E. M. Walton, S. L. McKnight, Science 253, 789–792 (1991). The data suggest that the protein encoded by λH1 and native NRSF have similar DNA-binding specificities as measured in this assay.

Immunological relatedness of recombinant and native NRSF. To obtain independent evidence for a relationship between native and recombinant NRSF, a mouse polyclonal antibody was generated against bacterially-expressed NRSF and tested for its ability to interact with native NRSD in an EMSA. The λH1 cDNA was inserted into the ExoRI site of pGEX-1, a prokaryotic glutathione S-transferase fusion expression vector [D. B. Smith and K. S. Johnson, Gene 67, 31 (1988)]. GST-λH1 fusion protein was partially purified by isolation of inclusion bodies. The inclusion body preparation was subjected to SDS-PAGE, gel slices containing the fusion protein were excised, mixed with adjuvant, and injected into mice. When the serum titer reached a sufficient level, a mycloma was injected into the peritoneum of the mouse, and a tumor was allowed to develop for 10 days. The polyclonal ascites fluid (Ou et al., J. Immunol. Meth. 165:75 (1993)) induced by this tumor was collected and clarified by centrifugation.

In a positive control experiment, the antibody was able to specifically supershift a portion of the λH1-encoded protein:DNA complex, while a control ascites was not (FIG. 4, lower panel; bracket, lanes 1–4). In HeLa cell nuclear extracts, the same antibody supershifted a portion of native NRSF complex (FIG. 4, upper panel; bracket, lanes 1–4). Furthermore, no supershift was seen with the control ascites (lanes 6–8) nor with several other control ascites (data not shown). The inability to obtain a complete supershift leaves open the possibility that HeLa nuclear extracts may contain multiple NRSE-binding proteins. Nevertheless, the antigenic similarity of the recombinant and native NRSF proteins provides further evidence that the cDNA clone encodes NRSF.

Example 2

Characterization of NRSF

Figure 5:
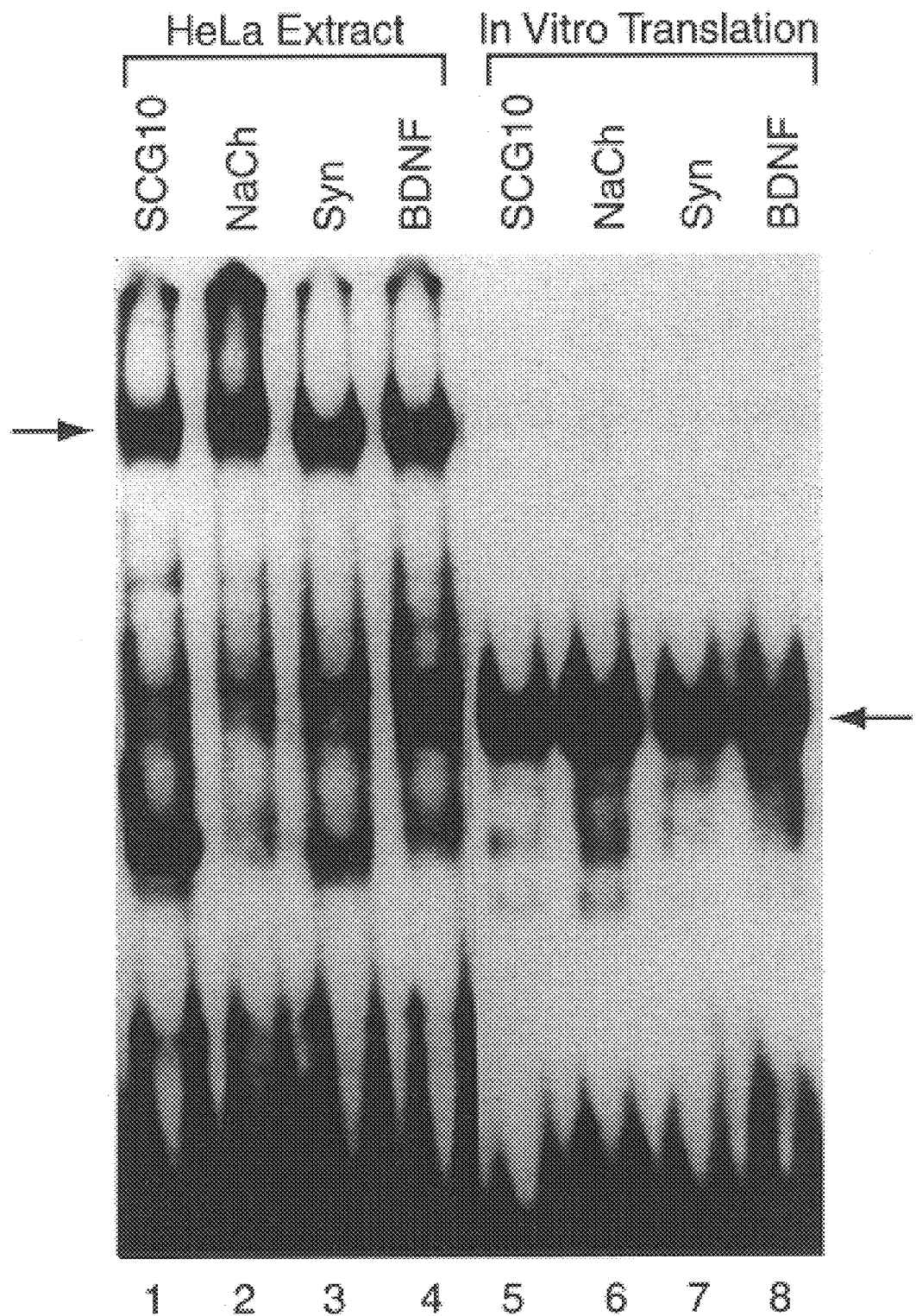
FIG. 5 shows that native and recombinant NRSF recognizes NRSE in four different neuron-specific genes. Electrophoretic mobility shift assays were preformed using either nuclear extract from HeLa cells (lanes 1–4), to reveal the activity of native NRSF, or using in vitro synthesized NRSF encoded by the λH1 cDNA (lanes 5–8). The labeled probes consisted of restriction fragments containing NRSEs derived for the rat SCG10 gene (SCG10, lanes 1–5); the rat type II sodium channel gene (NaCh, lanes 2 and 6); the human synapsis I gene (Syn, lanes 3 and 7) or the rat brain-derived neurotrophic factor gene (BDNF, lanes 4 and 8). The large arrowhead indicates the specific co-lex obtained with recombinant NRSF; small arrowhead that obtained with native NRSF. Note that the complexes obtained with all four probes are of similar sizes. The complexes obtained using HeLa extracts were partially supershifted with antibody to recombinant NRSF (cf.
Figures 7A, 7B:
FIGS. 7A and 7B. (A) Schematic diagram of the predicted amino acid sequences from the NRSF cDNA clones. λH1 is the original cDNA isolated by screening the HeLa expression library. λHZ4 was isolated by hybridization to λH1. (B) Alignment of NRSF zinc finger and interfinger sequences (SEQ ID NOS:41–48). The eight zinc fingers of human NRSF were aligned beginning with the conserved aromatic residue and including the interfinger sequences of fingers z2–7. The consensus for GLI-Krüppel zinc fingers and interfinger sequences is shown for comparison. The conserved tyrosinc residue is boxed.

NRSF interacts with NRSEs in multiple neuron-specific genes. NRSF-encoding cDNA clones were identified by virtue of their ability to bind to two independently-characterized functional NRSEs, one in the SCG10 gene, the other in the NaII channel gene. To determine whether NRSF also interacts with NRSE-like sequences identified in other neuron-specific genes, EMSAs were performed using probes containing potential NRSEs from the synapsin I and brain-derived neurotrophic factor (BDNF) genes. In the case of synapsin I, the NRSE-like sequence has been shown to function as a silencer by cell transfection assays (18) L. Li, T. Suzuki, N. Mori, P. Greengard, Proceedings of the National Academy of Science (USA) 90, 1460–1464 (1993). In the case of BDNF, the element was identified by sequence homology but has not yet been tested functionally (23) T. Timmusk, et al., Neuron 10, 475–489 (1993). Although BDNF is expressed both in neurons and in non-neuronal cells, this expression is governed by two sets of promoters which are separated by 15 kb; one set of the promoters is specifically utilized in neurons (23) T. Timmusk, et al., Neuron 10, 475–489 (1993). Native NRSF from HeLa cells yielded a specific complex of similar size using probes from all four genes (FIG. 5, lanes 1–4). At least a portion of all four of these complexes could be supershifted by the anti-NRSF antibody, and the SCG10 NRSE complex could be competed by oligonucleotides containing NRSEs from the other three genes (data not shown). Furthermore, all four probes also generated specific complexes with recombinant NRSF (FIG. 5, lanes 5–8). These data indicate that both native and recombinant NRSF are able to interact with consensus NRSEs in multiple neuron-specific genes.

NRSEs occur in many neuronal genes. Using a consensus NRSE derived from the four functionally-defined sequences (see above), the nucleotide sequence database was searched for related sequences. The Genbank database was searched using three different algorithms: Wordscarch and FastA from the GCG sequence analysis program [J. D. Devereux, P. Hacberli, O. Smithies, Necl. Acids Res. 12, 387 (1984)] and Blast [S. F. Altschul, W. Gish, W. Miller, E. W. Myers, D. J. Lipman, J. Mol. Biol. 215, 403 (1990)]. This search identified 13 additional neuronal genes that show, on average, 93% homology to the consensus NRSE (FIG. 1A). These genes include NMDA, ACh and glycine receptor subunits, neurofilament and neuronspecific tubulin. Moreover, in the six genes cloned from multiple species, both the sequence and intragenic location of the NRSEs are highly conserved (FIG. 1B) (SEQ ID NOS:15–28). This conservation of sequence and position in non-coding regions (which are frequently quite divergent between species), strongly suggests that these elements are functionally relevant to the transcription of these genes.

These database searches also revealed NRSE-like sequences in several non-neuronal genes (FIG. 1C) (SEQ ID NOS:29–38). The average percent similarity was only 84%, however, compared to 93% for the neuronal genes. Moreover, the average number of differences from the consensus NRSE is 3 bases for the non-neuronal genes, compared to 1.2 bases for the neuronal sequences. Thus, NRSF may not bind to all of these sequences, particularly those in which intragenic position is not conserved across species. However, we cannot exclude the possibility that NRSF may regulate some non-neuronal as well as neuronal genes.

NRSF cDNAs encode a novel protein with eight zinc fingers. To isolate longer NRSF cDNA clones, multiple cDNA libraries from human, mouse and rat were screened by hybridization with the λH1 clone. Five different cDNA libraries, derived from human HeLa cells, mouse 10T1/2 cells and rat brain were screened by plaque hybridization.

The selection of libraries included those made with inserts size-selected for length greater than 4 kb, as the estimated size of the NRSF mRNA on Northern blots is 8–9 kb. No cDNA isolated from any library extended past the 5' end of clone λHZ4, suggesting a possible strong stop to reverse transcriptase. Clones of similar size were isolated from both the human and mouse cDNA libraries.

The sequence of the longest clone obtained, λHZ4 (2.04 kb), is shown in FIG. 6 (SEQ ID NOS:39 and 40). λHZ4 has an open reading frame throughout its length with no candidate initiating methionine and no stop codon, indicating that the cDNA does not contain the full protein coding sequence for NRSF. Conceptual translation of the DNA sequence revealed that it contains a cluster of eight zinc fingers of the $C_2H_2$ class with interfinger sequences which place NRSF in the GLI-Krüppel family of zinc finger proteins (FIG. 5A, B) (26) R. Schuh, et al., Cell 47, 1025–1032 (1986); (27) J. M. Ruppert, et al., Molecular and Cellular Biology 8, 3104–3113 (1988). C-terminal to the zinc fingers is a 174 amino acid domain rich in lysine (26%; 46/174) and serine/threonine (21%; 37/174; FIG. 5A). A database search using the BLAST program did not reveal any sequences identical to λHZ4, indicating that NRSF represents a novel zinc finger protein (28) S. F. Altschul, W. Gish, W. Miller,. W. Myers, D. J. Lipman, Journal of Molecular Biology 215, 403–410 (1990). However, two different 'expressed sequence tags' likely to represent partial NRSF cDNAs were identified. High stringency Southern blot analysis of human, mouse and rat genomic DNA suggests that NRSF is a single copy gene (data not shown).

Repression of transcription by NRSF in vivo. To determine if the longest NRSF cDNA encoded a protein with transcriptional repressing activity, this cDNA (λHZ4) was cloned into the mammalian expression vector pCMV. PC12 cells were co-transfected with this NRSF expression construct and various target plasmids. One target plasmid (pCAT3-S36++) contained two copies of the NRSE inserted upstream of the SCG10 promoter, directing transcription of the bacterial chloramphenicol acetyltransferase (CAT) gene.

Control target plasmids contained either the proximal SCG10 promoter alone (pCAT3), or this promoter plus a mutant NRSE which cannot bind NRSF in vitro (pCAT3-Sm36) (15) N. Mori, S. Schoenherr, D. J. Vandenbergh, D. J Anderson, Neuron 9, 1–10 (1992).

To express NRSF in transient transfection experiments, the λHZ4 cDNA was inserted into the EcoRI site of pcDNA3-ATG, a modified form of pcDNA3 (invitrogen), a mammalian expression vector containing the cytomegalovirus enhancer and an oligonucleotide which provides a star codon in-frame with λHZ4 and a stop codon in all three reading frames. Transient transfections of PC12 cells were performed essentially as described. Each cotransfection included 5 μg of a reporter plasmid (pCAT3 or pCAT3-S36++), the expression plasmid (pCMV-1HZ4) at the concentrations indicated, pcDNA3-ATG to control for non-specific vector effects, 2 μg of pRSV-lacZ to normalize transfections and pBluescript to bring the total plasmid up to 10 μg. Cells were harvested 48 hr after transfection and processed for CAT and β-galactosidase assays as described [N. Mori, R. Stein, O'Sigmund, D. J. Anderson, Neuron 4, 583 (1990)], except CAT assays were quantified using a Molecular Dynamics Phosphor Imager.

Figure 8A:
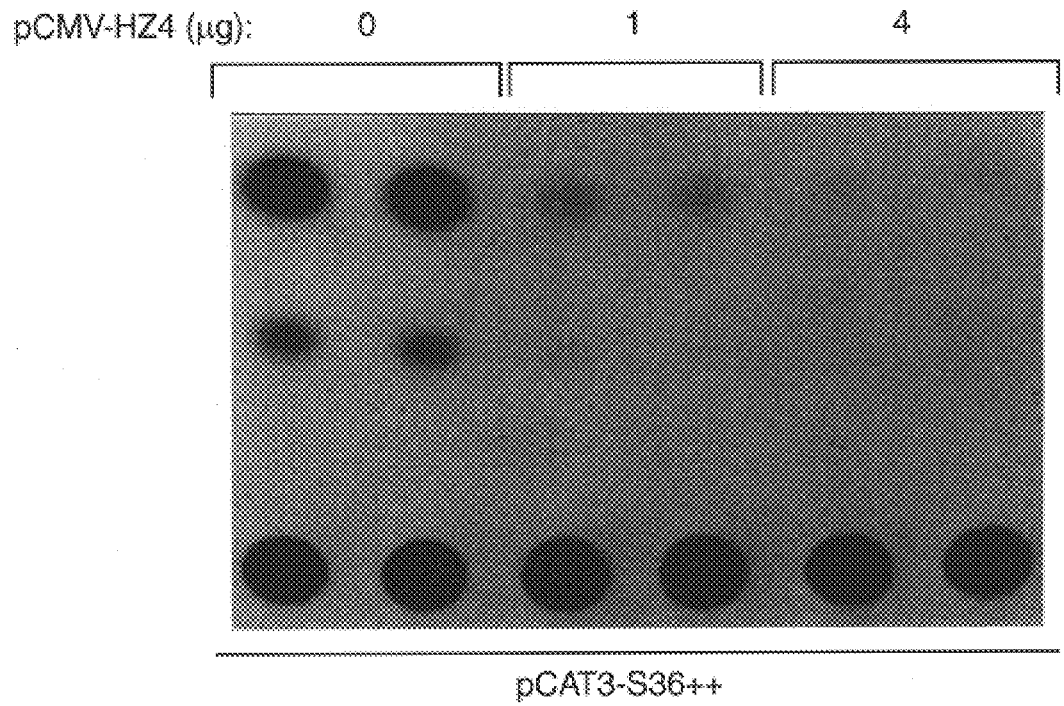
FIGS. 8A and 8B show the repression of transcription by recombinant NRSF. (A) A representative autoradiogram CAT enzymatic assays from cotransfection experiments in which increasing amounts of an expression plasmid (pCMV-HZ4) encoding a partial NRSF cDNA (clone λHZ4; see FIG. 7A) were cotransfected into PC12 cells together with a CAT reporter plasmid containing two tandem SCG10 NRSEs (pCAT3-S36++)(50). (B) A similar experiment as in (A) except that CAT reporter plasmid (pCAT3) lacked NRSEs. See FIG. 2 for quantification.
Figure 8B:
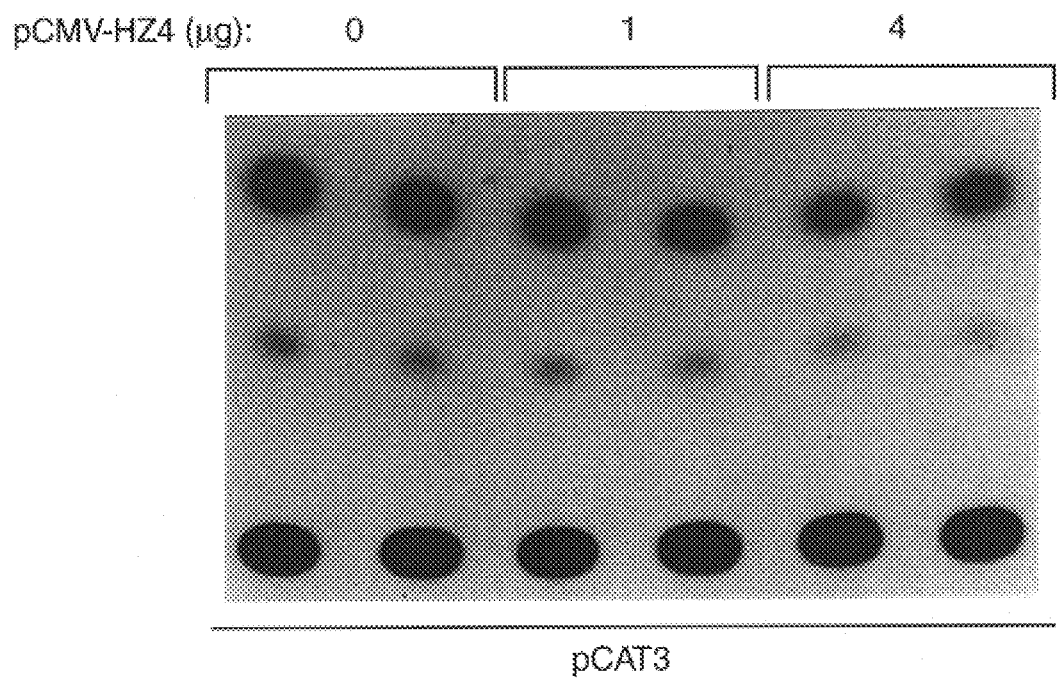

In transient, co-transfection experiments with pCAT3-S36++ and increasing amounts of pCMV-HZ4, transcription from the target plasmid was repressed from 11 to 32 fold (FIG. 8A; FIG. 2). In parallel transfections performed with pCAT3 as the reporter plasmid, only a modest decrease (1.5 fold at maximum pCMV-HZ4 concentration) in activity was seen with increasing amounts of pCMV-HZ4 (FIG. 8B; FIG. 2). Similar results were obtained with the target plasmid containing a mutated NRSE (data not shown). These results indicated that the λHZ4 clone contains at least a portion of the domain required for transcriptional repression, and that repression by cloned NRSF in vivo requires binding to the NRSE.

NRSF is expressed in neural progenitors but not in neurons. Previous work indicated that NRSE-dependent silencing activity and NRSE-binding activity are present only in non-neuronal cell lines and are absent from cell lines of neuronal origin (7) N. Mori, R. Stein, O. Sigmund, D. J. Anderson, Neurons 4, 583–594 (1990); (15) N. Mori, S. Schoenherr, D. J. Vandenbergh, D. J Anderson, Neuron 9, 1–10 (1992); (16) R. A. Maue, S. D. Knaner, R. H. Goodman, G. Mandel, Neuron 4, 223–231 (1990); (17) S. D. Kraner, J. A. Chong, H. J. Tsay, G. Mandel, Neuron 9, 37–44 (1992). The absence of these activities in neuronal cells could reflect a lack of NRSF gene expression; alternatively, NRSF might be expressed but be functionally inactive in neuronal cells. To distinguish between these possibilities, first RNase protection assayswere performed on several rodent neuronal and nonneuronal cell lines. RNase protections were performed as previously described [J. E. Johnson, K. Zimmerman, T. Saito, D. J. Anderson, Developnment 114, 75 (1992)] with minor modifications as indicated. The mouse NRSF riboprobe was created using T7 polymerase and a linearized subclone of the EcoRI-Eco47 III fragment frou 1M5 into the EcoRI and SmaI sites of pBluescript-KS. A rat β-actin riboprobe (gift of M-J. Fann and P. Patterson) was included in each reaction as a control for the amount and integrity of the RNA. Total cellular RNA was isolated as a control for the amount and integrity of the RNA. Total cellular RNA was isolated using the acid phenol method [P. Chomcynski, N. Sacchi, Anal. Biochem. 162, 156 (1987)].

Figure 9:
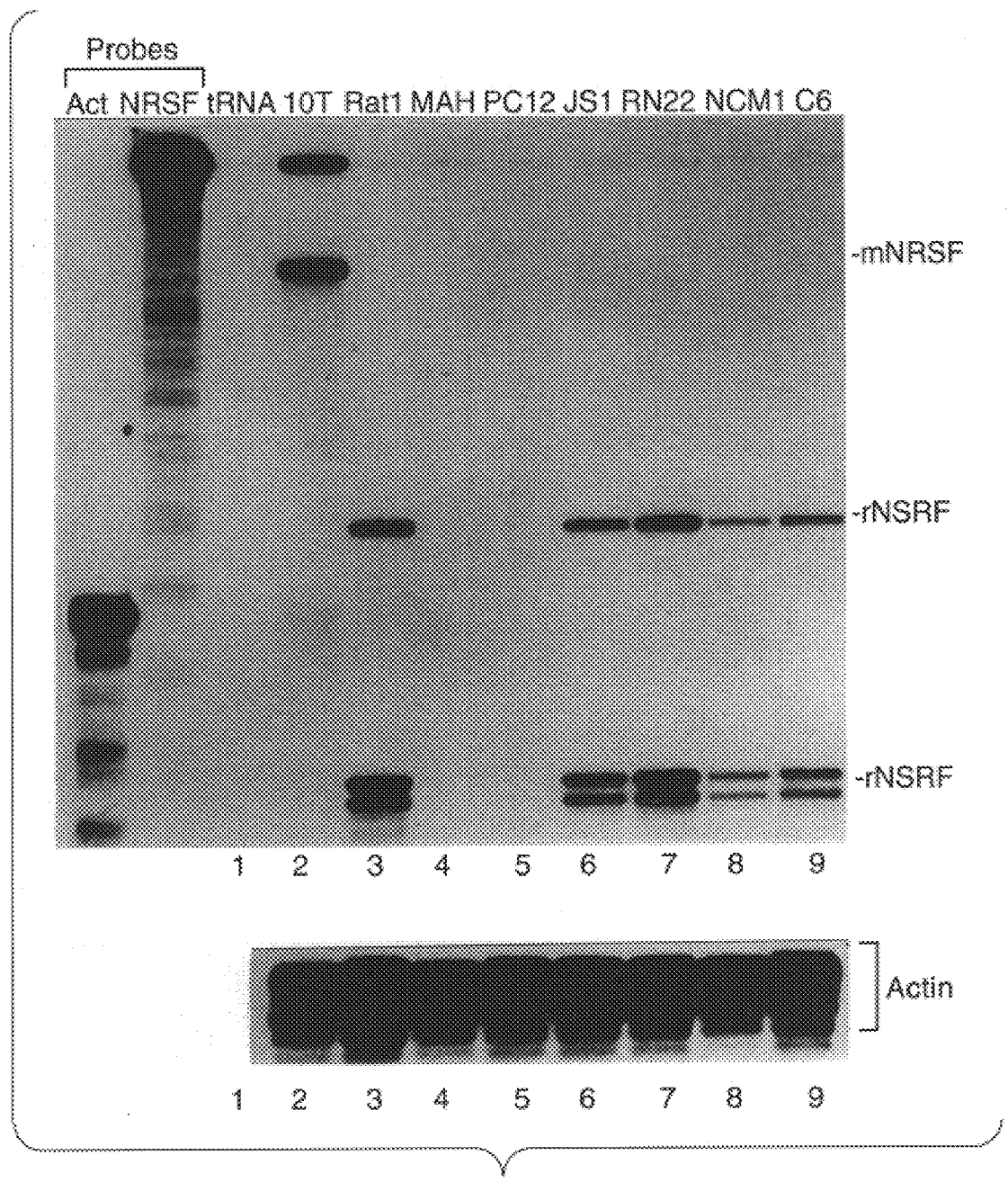
FIG. 9 depicts the analysis of NRSF message in neuronal and non-neuronal cell lines. RNase protections assays (51) were performed on 10 μg of total RNA from various cell lines. The two neuronal cell lines were MAH, an immortalized rat sympathoadrenal precursor (52), and PC12, a rat pheochromocytoma (53). The non-neuronal cell lines were: RN22 and JS-1, rat schwannomas (54) S. E. Pfeiffer, B. Betschart, J. Cook, P. E. Mancini, R. J. Morris, in *Glial cell lines* S. Federoff, L. Hertz, Eds. (Academic Press, New York, 1978) pp. 287–346; (55) H. Kimura, W. H. Fischer, D. Schubert, *Nature* 348, 257–260 (1990); NCM-1, an immortalized rat schwann cell precursor (56) L.-C. Lo, S. J. Birren, D. J. Anderson, *Devel. Biol.* 145, 139–153 (1990); C6, a rat CNS flioma (57) S. Kumar, et al., *J. Neurosci. Res.* 27, in press (1990); and RAT1 and mouse C3H1OT1/2(10T), embryonic fibroblast lines. A reaction containing yeast tRNA (tRNA) alone was preformed as a negative control. The probes were derived from mouse NRSF and rat β-actin cDNAs. rNRSF and mNRSF indicate the protected products obtained using RNA from rat or mouse cell lines, respectively. (The size difference between NRSF protected products of the mouse and rat most likely reflects a species difference in the sequence of the target mRNA, resulting in incomplete protection of the mouse probe by the rat transcript.) The autoradiographic exposure for the actin protected products was shorter than for NRSF. In this experiment, the RNase digestion was performed with RNase T1 only.

No NRSF transcripts were detectable in two neuronal cell lines, MAH and PC12 cells, which lack NRSE-binding activity in EMSAs (FIG. 9, lanes 4 and 5; rNRSF). In contrast, several rat cell lines of glial origin and two fibroblast lines expressed NRSF mRNA (FIG. 9, lanes 6–9). This pattern of expression is consistent with NRSFs proposed role as a negative regulator of neuron-specific gene expression in non-neuronal cells. Furthermore, the data imply that the absence of NRSF activity in neuronal cells is not due to functional inactivation of NRSF, but rather to the lack of NRSF expression.

In many parts of the embryonic nervous system, neurons and glia derive from multipotent progenitor cells (29) J. R. Sancs, Trends Neurosci. 12, 21–28 (1989); (30) R. D. G. McKay, Cell 58, 815–821 (1989); (31) S. K. McConnell, Ann. Rev. Neurosci. 14, 269–300 (1991). To determine whether such progenitor cells also express NRSF, in situ hybridization experiments on mouse embryos were performed. The morning of the day of detection of a vaginal plug was designated as embryonic day 0.5. Fixation, embedding, sectioning, preparation of digoxygenin-labeled cRNA probes and in situ hybridization with nonradioactive detection were performed as described [S. J. Birren, L. C. Lo, D. J. Anderson, *Development* 119, 507 (1993)]. Both sense and antisense probes for NRSF were generated from linearized plasmid excised from the λM5 EXlox phage using a Cre recombinase system (Novagen). The antisense SCG10 probe has been described elsewhere [R. Stein, N. Mori, K. Matthes, L. Lo, D. J. Anderson, *Neruon* 1, 463 (1988)].

Figure 10A:
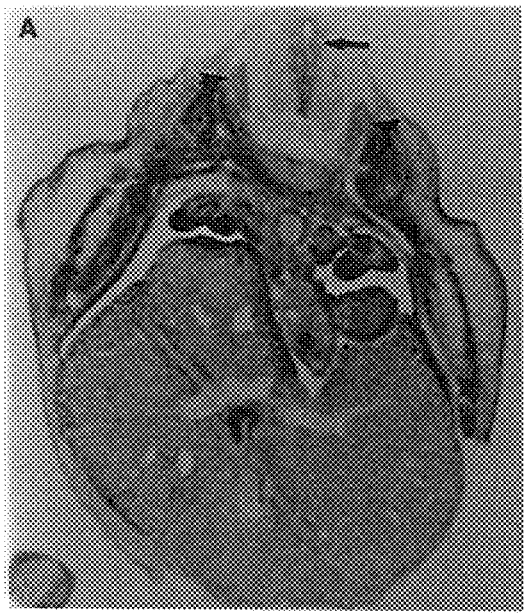
FIGS. 10A, 10B, 10C and 10D depict the comparison of NRSF and SCG10 mRNA expression by in situ hybridization. Adjacent transverse sections of E12.5 (A,B) and E13.5 (C,D) mouse embryos were hybridized with NRSF (A,C) or SCG10 (B,D) antisence probes. The arrows (A–D) indicate the ventricular zone of the neural tube. The large arrowheads (A–D) indicate the sensory ganglia and the small arrowheads, the sympathetic ganglia (C and D). Control hybridization with NRSF sense probes revealed no specific signal (FIG. 9C and data not shown).
Figure 10B:
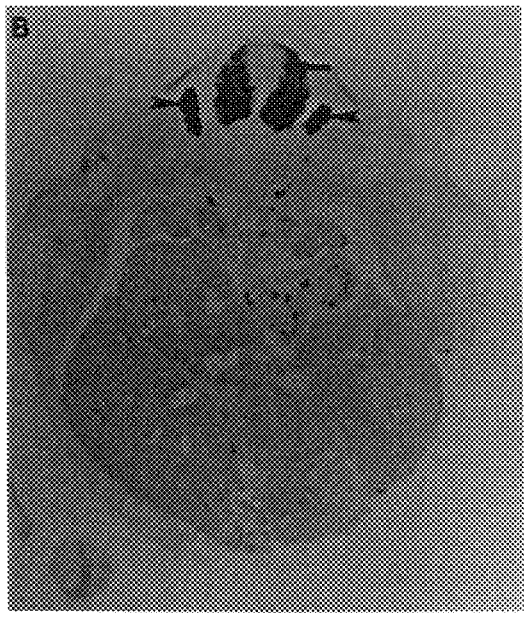
Figure 10C:
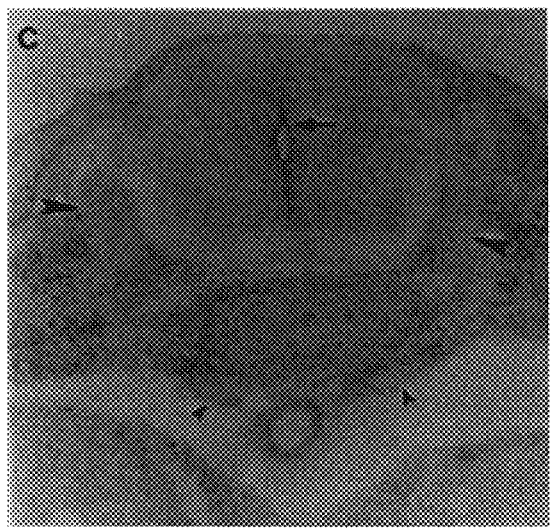
Figure 11A:
FIGS. 11A, 11B and 11C depict the widespread expession of NRSF mRNA in non-neural tissues. In situ hybridization with an NRSF antisense probe (A,B) was performed on parasaggital sections of an E13.5 mouse embryo. (A) The arrowheads mark two positive tissues, the lung and the kidney; the arrow indicates the liver, which expresses much lower levels of NRSF mRNA (see also FIG. 9). (B) The arrowhead marks the ventricular zone in the telencephalon, the arrow indicates the heart. (C) An adjacent section to (B) was hybridized with an NRSF sense probe as a control for non-specific staining (59).
Figure 11B:
Figure 11C:

In transverse sections of E12.5 mouse embryos, NRSF hybridization was detected in the ventricular zone of the neural tube (FIG. 10A, arrow), a region containing mitotically active multipotential progenitors of neurons and glia (32) S. M. Leber, S. M. Breedlove, J. R. Sanes, *J. Neurosci.* 10, 2451–2462 (1990) which do not express SCG10 mRNA (compare FIG. 10B, arrow). In contrast, the adjacent marginal zone of the neural tube which contains SCG10 positive neurons (FIG. 10B) was largely devoid of NRSF expression (FIG. 10A). A similar complementarity of NRSF and SCG10 expression in the neural tube was detected at E13.5 (FIGS. 10C, D; arrows), when the marginal zone has expanded. NRSF mRNA was also detected in the ventricular zone of the forebrain (FIG. 11B, arrowhead).

Figure 10D:
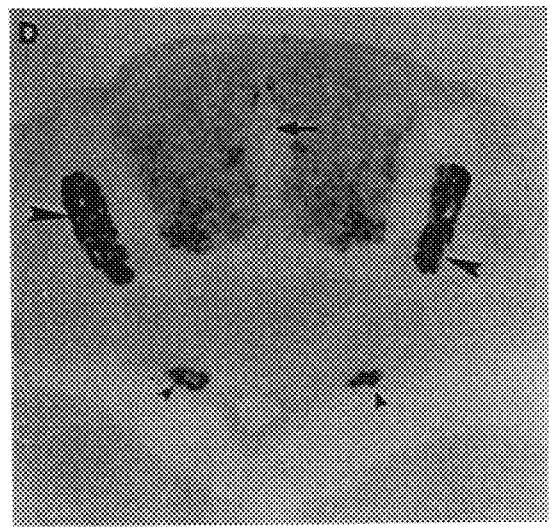

In the peripheral nervous system, NRSF mRNA was absent or expressed at low levels in sympathetic and dorsal root sensory ganglia (DRG) at E13.5 (FIG. 10C, small and large arrowheads) whereas these ganglia clearly expressed SCG10 mRNA (FIG. 10D, small and large arrowheads). At E12.5, the DRG appeared to express higher levels of NRSF mRNA than the marginal zone of the neural tube (FIG. 10A, arrowheads). This NRSF expression may derive from undifferentiated neural crest cells that are present in DRG at these early developmental stages. Taken together, these data suggest that NRSF is expressed by undifferentiated neuronal progenitors but not by differentiated (SCG10+) neurons in vivo.

Widespread expression of NRSF in non-neural tissues. Previous experiments in transgenic mice suggested that the NRSE is required to prevent SCG10 expression in multiple non-neural tissues throughout development (8) C. W. Wuenschell, N. Mori, D. J. Anderson, *Neuron* 4, 595–602 (1990). To determine whether this broad requirement for the NRSE element is reflected in a broad expression of NRSF, we examined its expression in non-neuronal tissues by in situ hybridization experiments. These experiments revealed NRSF mRNA expression in many non-neural tissues such as the adrenal gland, aorta, genital tubercle, gut, kidney, lung, ovaries, pancreas, parathyroid gland, skeletal muscle, testes, thymus, tongue, and umbilical cord (FIGS. 11A, B and data not shown). NRSF mRNA was also detected in a variety of adult non-neuronal tissues by RNase protection (data not shown). This broad expression pattern is consistent with a role for NRSF as a ncar-ubiquitous negative regulator of neuron-specific gene expression.

NRSF coordinately represses multiple neuron-specific target genes. The present finding that many neuron-specific genes are coordinately repressed by a common silencer factor stands in apparent contrast to the cases of most other tissue-specific genes studied previously in higher vertebrates. In these cases, repression in non-expressing tissues is accomplished by both the absence of lineage-specific enhancer factors (12) P. Mitchell, R. Tjian, *Science* 245, 371–378 (1989); (13) P. F. Johnson, S. L. McKnight, *Annu. Rev. Biochem.* 58, 799–839 (1989), and by assembly into transcriptionally-inactive chromatin (43) H. Weintraub, *Cell* 42, 705–711 (1985). While silencer factors have been implicated in the regulation of other cell type-specific genes in higher vertebrates, they appear to function primarily to achieve differential expression between closely-related cell types or developmental stages using common lineage-specific enhancers (35) A. Winoto, D. Baltimore, *Cell*, 59, 649–665 (1989); (36) S. A. Camper, S. M. Tilghman, *Genes Dev.* 3, 537–546 (1989); (37) M. Sheng, M. E. Greenberg, *Neuron* 4, 477–485 (1990); (38) P. Savagner, T. Miyashita, Y. Yamada, *J. Biol. Chem.* 265, 6669–6674 (1990); (39) R. Shen, S. K. Goswami, E. Mascareno, A. Kumar, M. A. Q. Siddiqui, *Mol. Cell. Biol.*, 11, 1676–1685 (1991); (40) S. Sawada, J. D. Scarborough, N. Killeen, D. R. Littman, *Cell* 77, 917–929 (1994). In contrast, the coordinate cell type-specific silencing mediated by NRSF seems more analogous to MATα2 in yeast, which coordinates repression of multiple a-specific genes in α cells (41) I. Herskowitz, *Nature* 342, 749–757 (1989), or to the Drosophila Polycomb genes, which negatively regulate several homeotic genes (42) R. Paro, *Trends in Genetics* 6, 416–421 (1990). The identification of NRSF suggests that coordinate repression of cell-type specific genes may be an alternative mechanism for achieving the differential expression of cell type- or lineage-specific genes in higher vertebrates.

Possible role of NRSF in neurogenesis. In other systems, positive-acting transcription factors that coordinately regulate multiple lineage-specific target genes have been shown to function as master regulators of cell type determination or differentiation (1) L. M. Corcoran, et al., *Genes and Development* 7, 570–582 (1993); (3) L. Pevny, et al., *Nature* 349, 257–260 (1991); (33) H. Weintraub, et al., *Science* 251, 761–766 (1991); (44) S. Li, et al., *Nature* 347: 528–533 (1990). By analogy, NRSF may play a key role in the selection or expression of a neuronal phenotype. As a first step towards determining the role of NRSF in neurogenesis, the expression pattern of NRSF during embryonic development was examined by in situ hybridization. These data indicate that NRSF is undetectable or expressed at low levels in neurons, but is expressed in regions of the embryonic CNS that contain neuronal precursors. Consistent with this, abundant expression of NRSF mRNA was detected in undifferentiated P19 cells, a murine embryonal carcinoma cell line that can differentiate into neurons when cultured with retinoic acid (unpublished data). The presence of NRSF in neuronal progenitors, together with its proposed coordinate negative regulation of many neuronal genes, suggests that relief from NRSF-imposed repression may be a key event in either neuronal determination or differentiation. In either case, the absence of NRSF mRNA in neurons indicates that this derepression most likely occurs by an extinction of NRSF expression, rather than by its functional inactivation. Such a mechanism implies that neuronal precursors are actively prevented from differentiating until released from this repression by a signal that extinguishes NRSF expression. This idea has intriguing parallels to mechanisms recently shown to underlie neural induction in Xenopus embryos. In that system ectodermal cells are apparently actively prevented from adopting a neural fate by activin, and can undergo neural induction only after a relief from this repression by follistatin, an inhibitor of activin (45) A. Hemmati-Brivanlou, O. G. Kelly, D. A. Melton, *Cell* 77, 283–295 (1994); (46) A. Hemmati-Brivanlou, D. A. Melton, Cell 77, 273–281 (1994). It remains to be determined whether the action of follistatin is in any related to the activity or expression of NRSF. In any case, the identification of NRSF provides an opportunity to further understand the control of an apparently central event in neurogenesis.

We claim:

1. An isolated recombinant nucleic acid encoding a protein comprising the amino acid sequence shown in FIG. 6 (SEQ ID NO:40).

2. The nucleic acid of claim 1 comprising the nucleotide sequence shown in FIG. 6 (SEQ ID NO:39).

3. An expression vector comprising transcriptional and translational regulatory nucleic acid operably linked to nucleic acid encoding a protein comprising the amino acid sequence shown in FIG. 6 (SEQ ID NO:40).

4. An expression vector comprising transcriptional and translational regulatory nucleic acid operably linked to nucleic acid comprising the nucleotide sequence shown in FIG. 6 (SEQ ID NO:39).

5. A host cell transformed with an expression vector comprising a nucleic acid encoding a protein comprising the amino acid sequence shown in FIG. 6 (SEQ ID NO:40).

6. A host cell transformed with an expression vector comprising the sequence shown in FIG. 6 (SEQ ID NO:39).

7. A method of producing a protein comprising:

a) culturing a host cell transformed with an expressing vector comprising a nucleic acid encoding a protein comprising the amino acid sequence shown in FIG. 6 (SEQ ID NO:40); and b) expressing said nucleic acid to produce a protein, wherein said protein surpresses the expression of neuronal genes.

* * * * *

SEQUENCE LISTING (1) GENERAL INFORMATION:

(iii) NUMBER OF SEQUENCES: 53

(2) INFORMATION FOR SEQ ID NO:1:

(i) SEQUENCE CHARACTERISTICS:
      (A) LENGTH: 31 base pairs
      (B) TYPE: nucleic acid
      (C) STRANDEDNESS: unknown
      (D) TOPOLOGY: unknown (ii) MOLECULE TYPE: cDNA (ix) FEATURE:
      (A) NAME/KEY: misc_feature
      (B) LOCATION: 1..31
      (D) OTHER INFORMATION: /note= "SCG10"

(xi) SEQUENCE DESCRIPTION: SEQ ID NO:1:

GCCATTTCAG CACCNCGGAG AGNGCCTCTG C                     31

(2) INFORMATION FOR SEQ ID NO:2:

(i) SEQUENCE CHARACTERISTICS:
      (A) LENGTH: 31 base pairs
      (B) TYPE: nucleic acid
      (C) STRANDEDNESS: unknown
      (D) TOPOLOGY: unknown (ii) MOLECULE TYPE: cDNA (ix) FEATURE:
      (A) NAME/KEY: misc_feature
      (B) LOCATION: 1..31
      (D) OTHER INFORMATION: /note= "Na Channel"

(xi) SEQUENCE DESCRIPTION: SEQ ID NO:2:

TGGGTTTCAG AACCNCGGAC AGNACCAGAG T                     31

(2) INFORMATION FOR SEQ ID NO:3:

(i) SEQUENCE CHARACTERISTICS:
      (A) LENGTH: 31 base pairs
      (B) TYPE: nucleic acid
      (C) STRANDEDNESS: unknown
      (D) TOPOLOGY: unknown (ii) MOLECULE TYPE: DNA (genomic)

(ix) FEATURE:
      (A) NAME/KEY: misc_feature
      (B) LOCATION: 1..31
      (D) OTHER INFORMATION: /note= "Synapsin I"

(xi) SEQUENCE DESCRIPTION: SEQ ID NO:3:

CCAGCTTCAG CACCNCGGAG AGNGCCTTCG C                     31

(2) INFORMATION FOR SEQ ID NO:4:

(i) SEQUENCE CHARACTERISTICS:
      (A) LENGTH: 31 base pairs
      (B) TYPE: nucleic acid
      (C) STRANDEDNESS: unknown
      (D) TOPOLOGY: unknown (ii) MOLECULE TYPE: cDNA (ix) FEATURE:
        (A) NAME/KEY: misc_feature
        (B) LOCATION: 1..31
        (D) OTHER INFORMATION: /note= "BDNF"

(xi) SEQUENCE DESCRIPTION: SEQ ID NO:4:

GTCCATTCAG CACCNTGGAG AGNGCCAGCG G                                    31

(2) INFORMATION FOR SEQ ID NO:5:

(i) SEQUENCE CHARACTERISTICS:
        (A) LENGTH: 31 base pairs
        (B) TYPE: nucleic acid
        (C) STRANDEDNESS: unknown
        (D) TOPOLOGY: unknown (ii) MOLECULE TYPE: cDNA (ix) FEATURE:
        (A) NAME/KEY: misc_feature
        (B) LOCATION: 1..31
        (D) OTHER INFORMATION: /note= "Glycine Receptr(rev)"

(xi) SEQUENCE DESCRIPTION: SEQ ID NO:5:

GGCGTTTCAG CACCNCGGAG AGNGTCCAGA C                                    31

(2) INFORMATION FOR SEQ ID NO:6:

(i) SEQUENCE CHARACTERISTICS:
        (A) LENGTH: 31 base pairs
        (B) TYPE: nucleic acid
        (C) STRANDEDNESS: unknown
        (D) TOPOLOGY: unknown (ii) MOLECULE TYPE: cDNA (ix) FEATURE:
        (A) NAME/KEY: misc_feature
        (B) LOCATION: 1..31
        (D) OTHER INFORMATION: /note= "NMDA Receptor"

(xi) SEQUENCE DESCRIPTION: SEQ ID NO:6:

CCCGCTTCAG CACCNCGGAG AGNGCCGGCC G                                    31

(2) INFORMATION FOR SEQ ID NO:7:

(i) SEQUENCE CHARACTERISTICS:
        (A) LENGTH: 31 base pairs
        (B) TYPE: nucleic acid
        (C) STRANDEDNESS: unknown
        (D) TOPOLOGY: unknown (ii) MOLECULE TYPE: cDNA (ix) FEATURE:
        (A) NAME/KEY: misc_feature
        (B) LOCATION: 1..31
        (D) OTHER INFORMATION: /note= "ACH Recptr B2"

(xi) SEQUENCE DESCRIPTION: SEQ ID NO:7:

GCGGCTTCAG CACCNCGGAG AGNGCCCCAC C                                    31

(2) INFORMATION FOR SEQ ID NO:8:

(i) SEQUENCE CHARACTERISTICS:
        (A) LENGTH: 31 base pairs
        (B) TYPE: nucleic acid
        (C) STRANDEDNESS: unknown
        (D) TOPOLOGY: unknown (ii) MOLECULE TYPE: cDNA (ix) FEATURE:
              (A) NAME/KEY: misc_feature
              (B) LOCATION: 1..31
              (D) OTHER INFORMATION: /note= "Neurofilament-M"

(xi) SEQUENCE DESCRIPTION: SEQ ID NO:8:

GGGGTTTCAG CACCNCGGAG AGNTCCCGCG G                                            31

(2) INFORMATION FOR SEQ ID NO:9:

(i) SEQUENCE CHARACTERISTICS:
              (A) LENGTH: 31 base pairs
              (B) TYPE: nucleic acid
              (C) STRANDEDNESS: unknown
              (D) TOPOLOGY: unknown (ii) MOLECULE TYPE: cDNA (ix) FEATURE:
              (A) NAME/KEY: misc_feature
              (B) LOCATION: 1..31
              (D) OTHER INFORMATION: /note= "B-4 Tubulin"

(xi) SEQUENCE DESCRIPTION: SEQ ID NO:9:

CGCCGTTCAG CACCNCGGAG AGNGCCGCCT G                                            31

(2) INFORMATION FOR SEQ ID NO:10:

(i) SEQUENCE CHARACTERISTICS:
              (A) LENGTH: 31 base pairs
              (B) TYPE: nucleic acid
              (C) STRANDEDNESS: unknown
              (D) TOPOLOGY: unknown (ii) MOLECULE TYPE: cDNA (ix) FEATURE:
              (A) NAME/KEY: misc_feature
              (B) LOCATION: 1..31
              (D) OTHER INFORMATION: /note= "Cort. Releasing Fctr."

(xi) SEQUENCE DESCRIPTION: SEQ ID NO:10:

GGCGCTTCAG CACCNCGGAG AGNGCCCATC C                                            31

(2) INFORMATION FOR SEQ ID NO:11:

(i) SEQUENCE CHARACTERISTICS:
              (A) LENGTH: 31 base pairs
              (B) TYPE: nucleic acid
              (C) STRANDEDNESS: unknown
              (D) TOPOLOGY: unknown (ii) MOLECULE TYPE: cDNA (ix) FEATURE:
              (A) NAME/KEY: misc_feature
              (B) LOCATION: 1..31
              (D) OTHER INFORMATION: /note= "Calbindin"

(xi) SEQUENCE DESCRIPTION: SEQ ID NO:11:

GCACAGTCAG CACCNCGGAG AGNGCCCCCG C                                            31

(2) INFORMATION FOR SEQ ID NO:12:

(i) SEQUENCE CHARACTERISTICS:
              (A) LENGTH: 31 base pairs
              (B) TYPE: nucleic acid
              (C) STRANDEDNESS: unknown
              (D) TOPOLOGY: unknown

```
    (ii) MOLECULE TYPE: cDNA (ix) FEATURE:
         (A) NAME/KEY: misc_feature
         (B) LOCATION: 1..31
         (D) OTHER INFORMATION: /note= "Synaptotagmin-4"

(xi) SEQUENCE DESCRIPTION: SEQ ID NO:12:

GTTCTTTCAG CACCNCGGAG AGNGCACGCA G                                          31

(2) INFORMATION FOR SEQ ID NO:13:

(i) SEQUENCE CHARACTERISTICS:
         (A) LENGTH: 31 base pairs
         (B) TYPE: nucleic acid
         (C) STRANDEDNESS: unknown
         (D) TOPOLOGY: unknown (ii) MOLECULE TYPE: cDNA (ix) FEATURE:
         (A) NAME/KEY: misc_feature
         (B) LOCATION: 1..31
         (D) OTHER INFORMATION: /note= "HES-3"

(xi) SEQUENCE DESCRIPTION: SEQ ID NO:13:

GGGCAGGCAG CACCNCGGAG AGNGCCAACC C                                          31

(2) INFORMATION FOR SEQ ID NO:14:

(i) SEQUENCE CHARACTERISTICS:
         (A) LENGTH: 31 base pairs
         (B) TYPE: nucleic acid
         (C) STRANDEDNESS: unknown
         (D) TOPOLOGY: unknown (ii) MOLECULE TYPE: cDNA (ix) FEATURE:
         (A) NAME/KEY: misc_feature
         (B) LOCATION: 1..31
         (D) OTHER INFORMATION: /note= "Synaptophysin"

(xi) SEQUENCE DESCRIPTION: SEQ ID NO:14:

CGCGCTCCAG CACCNTGGAG AGNGCCCGGC G                                          31

(2) INFORMATION FOR SEQ ID NO:15:

(i) SEQUENCE CHARACTERISTICS:
         (A) LENGTH: 21 base pairs
         (B) TYPE: nucleic acid
         (C) STRANDEDNESS: unknown
         (D) TOPOLOGY: unknown (ii) MOLECULE TYPE: cDNA (ix) FEATURE:
         (A) NAME/KEY: misc_feature
         (B) LOCATION: 1..21
         (D) OTHER INFORMATION: /note= "Human Calbindin"

(xi) SEQUENCE DESCRIPTION: SEQ ID NO:15:

AGCAGCACCN AGGAGAGNGC C                                                     21

(2) INFORMATION FOR SEQ ID NO:16:

(i) SEQUENCE CHARACTERISTICS:
         (A) LENGTH: 21 base pairs
         (B) TYPE: nucleic acid
         (C) STRANDEDNESS: unknown
         (D) TOPOLOGY: unknown
```

```
    (ii) MOLECULE TYPE: cDNA (ix) FEATURE:
         (A) NAME/KEY: misc_feature
         (B) LOCATION: 1..21
         (D) OTHER INFORMATION: /note= "Chicken Calbindin"

(xi) SEQUENCE DESCRIPTION: SEQ ID NO:16:

GTCAGCACCN CGGAGAGNGC C                                                   21

(2) INFORMATION FOR SEQ ID NO:17:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown (ii) MOLECULE TYPE: cDNA (ix) FEATURE:
         (A) NAME/KEY: misc_feature
         (B) LOCATION: 1..21
         (D) OTHER INFORMATION: /note= "Rat Calbindin"

(xi) SEQUENCE DESCRIPTION: SEQ ID NO:17:

AGCAGCACCN CGGAGAGNGC C                                                   21

(2) INFORMATION FOR SEQ ID NO:18:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown (ii) MOLECULE TYPE: cDNA (ix) FEATURE:
         (A) NAME/KEY: misc_feature
         (B) LOCATION: 1..21
         (D) OTHER INFORMATION: /note= "Mouse Calbindin"

(xi) SEQUENCE DESCRIPTION: SEQ ID NO:18:

AGCAGCACCN CGGAGAGNGC C                                                   21

(2) INFORMATION FOR SEQ ID NO:19:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown (ii) MOLECULE TYPE: cDNA (ix) FEATURE:
         (A) NAME/KEY: misc_feature
         (B) LOCATION: 1..21
         (D) OTHER INFORMATION: /note= "Human CRF"

(xi) SEQUENCE DESCRIPTION: SEQ ID NO:19:

TTCAGCACCN CGGAGAGNGC C                                                   21

(2) INFORMATION FOR SEQ ID NO:20:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown
```

(ii) MOLECULE TYPE: cDNA (ix) FEATURE:
    (A) NAME/KEY: misc_feature
    (B) LOCATION: 1..21
    (D) OTHER INFORMATION: /note= "Rat CRF"

(xi) SEQUENCE DESCRIPTION: SEQ ID NO:20:

TTCAGCACCN CGGAGAGNGT C                                              21

(2) INFORMATION FOR SEQ ID NO:21:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown (ii) MOLECULE TYPE: cDNA (ix) FEATURE:
        (A) NAME/KEY: misc_feature
        (B) LOCATION: 1..21
        (D) OTHER INFORMATION: /note= "Sheep CRF"

(xi) SEQUENCE DESCRIPTION: SEQ ID NO:21:

TTCAGCACTN CGGAGAGNGC C                                              21

(2) INFORMATION FOR SEQ ID NO:22:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown (ii) MOLECULE TYPE: cDNA (ix) FEATURE:
        (A) NAME/KEY: misc_feature
        (B) LOCATION: 1..21
        (D) OTHER INFORMATION: /note= "Xenopus CRF"

(xi) SEQUENCE DESCRIPTION: SEQ ID NO:22:

TTCAGCACCN CGGAGAGNGA A                                              21

(2) INFORMATION FOR SEQ ID NO:23:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown (ii) MOLECULE TYPE: cDNA (ix) FEATURE:
        (A) NAME/KEY: misc_feature
        (B) LOCATION: 1..21
        (D) OTHER INFORMATION: /note= "Human Neuronal NIC ACHR B-2"

(xi) SEQUENCE DESCRIPTION: SEQ ID NO:23:

TTCAGCACCN CGGAGAGNGC C                                              21

(2) INFORMATION FOR SEQ ID NO:24:

(i) SEQUENCE CHARACTERISTICS:
        (A) LENGTH: 21 base pairs
        (B) TYPE: nucleic acid
        (C) STRANDEDNESS: unknown
        (D) TOPOLOGY: unknown (ii) MOLECULE TYPE: cDNA (ix) FEATURE:
            (A) NAME/KEY: misc_feature
            (B) LOCATION: 1..21
            (D) OTHER INFORMATION: /note= "Rat Neuronal NIC. ACHR B-2"

(xi) SEQUENCE DESCRIPTION: SEQ ID NO:24:

TTCAGCACCN CGGAGAGNGT C                                              21

(2) INFORMATION FOR SEQ ID NO:25:

(i) SEQUENCE CHARACTERISTICS:
            (A) LENGTH: 21 base pairs
            (B) TYPE: nucleic acid
            (C) STRANDEDNESS: unknown
            (D) TOPOLOGY: unknown (ii) MOLECULE TYPE: cDNA (ix) FEATURE:
            (A) NAME/KEY: misc_feature
            (B) LOCATION: 1..21
            (D) OTHER INFORMATION: /note= "Human NMDAR (NR1-1)"

(xi) SEQUENCE DESCRIPTION: SEQ ID NO:25:

TTCAGCACCN CGGAGAGNGC C                                              21

(2) INFORMATION FOR SEQ ID NO:26:

(i) SEQUENCE CHARACTERISTICS:
            (A) LENGTH: 21 base pairs
            (B) TYPE: nucleic acid
            (C) STRANDEDNESS: unknown
            (D) TOPOLOGY: unknown (ii) MOLECULE TYPE: cDNA (ix) FEATURE:
            (A) NAME/KEY: misc_feature
            (B) LOCATION: 1..21
            (D) OTHER INFORMATION: /note= "Rat NMDAR (NR1-1)"

(xi) SEQUENCE DESCRIPTION: SEQ ID NO:26:

TTCAGCACCN CGGAGAGNAT C                                              21

(2) INFORMATION FOR SEQ ID NO:27:

(i) SEQUENCE CHARACTERISTICS:
            (A) LENGTH: 21 base pairs
            (B) TYPE: nucleic acid
            (C) STRANDEDNESS: unknown
            (D) TOPOLOGY: unknown (ii) MOLECULE TYPE: cDNA (ix) FEATURE:
            (A) NAME/KEY: misc_feature
            (B) LOCATION: 1..21
            (D) OTHER INFORMATION: /note= "Human Synapsin I"

(xi) SEQUENCE DESCRIPTION: SEQ ID NO:27:

TTCAGCACCN CGGAGAGNGC C                                              21

(2) INFORMATION FOR SEQ ID NO:28:

(i) SEQUENCE CHARACTERISTICS:
            (A) LENGTH: 21 base pairs
            (B) TYPE: nucleic acid
            (C) STRANDEDNESS: unknown
            (D) TOPOLOGY: unknown (ii) MOLECULE TYPE: cDNA (ix) FEATURE:
             (A) NAME/KEY: misc_feature
             (B) LOCATION: 1..21
             (D) OTHER INFORMATION: /note= "Rat Synapsin I"

(xi) SEQUENCE DESCRIPTION: SEQ ID NO:28:

TTTAGTACCN CGGAGAGNGC C                                                    21

(2) INFORMATION FOR SEQ ID NO:29:

(i) SEQUENCE CHARACTERISTICS:
             (A) LENGTH: 31 base pairs
             (B) TYPE: nucleic acid
             (C) STRANDEDNESS: unknown
             (D) TOPOLOGY: unknown (ii) MOLECULE TYPE: cDNA (ix) FEATURE:
             (A) NAME/KEY: misc_feature
             (B) LOCATION: 1..31
             (D) OTHER INFORMATION: /note= "Som. Act. Fctr. (rev)"

(xi) SEQUENCE DESCRIPTION: SEQ ID NO:29:

GTTCTTTCAG CACCNCGGAG AGNGCACGCA G                                          31

(2) INFORMATION FOR SEQ ID NO:30:

(i) SEQUENCE CHARACTERISTICS:
             (A) LENGTH: 31 base pairs
             (B) TYPE: nucleic acid
             (C) STRANDEDNESS: unknown
             (D) TOPOLOGY: unknown (ii) MOLECULE TYPE: cDNA (ix) FEATURE:
             (A) NAME/KEY: misc_feature
             (B) LOCATION: 1..31
             (D) OTHER INFORMATION: /note= "NCAM"

(xi) SEQUENCE DESCRIPTION: SEQ ID NO:30:

GCGATTTCAG CACCNGGGAG AGNGAACCTG G                                          31

(2) INFORMATION FOR SEQ ID NO:31:

(i) SEQUENCE CHARACTERISTICS:
             (A) LENGTH: 31 base pairs
             (B) TYPE: nucleic acid
             (C) STRANDEDNESS: unknown
             (D) TOPOLOGY: unknown (ii) MOLECULE TYPE: cDNA (ix) FEATURE:
             (A) NAME/KEY: misc_feature
             (B) LOCATION: 1..31
             (D) OTHER INFORMATION: /note= "Atrial Natriuretic Peptide"

(xi) SEQUENCE DESCRIPTION: SEQ ID NO:31:

TAAACTTCAG CACCNAGGAG AGNCGCCGAG G                                          31

(2) INFORMATION FOR SEQ ID NO:32:

(i) SEQUENCE CHARACTERISTICS:
             (A) LENGTH: 31 base pairs
             (B) TYPE: nucleic acid
             (C) STRANDEDNESS: unknown
             (D) TOPOLOGY: unknown (ii) MOLECULE TYPE: cDNA (ix) FEATURE:
         (A) NAME/KEY: misc_feature
         (B) LOCATION: 1..31
         (D) OTHER INFORMATION: /note= "Rat APRT (rev)"

(xi) SEQUENCE DESCRIPTION: SEQ ID NO:32:

GCTGAGTCAG GACCNTGGAG AGNGCCTGAC C                                        31

(2) INFORMATION FOR SEQ ID NO:33:

(i) SEQUENCE CHARACTERISTICS:
        (A) LENGTH: 31 base pairs
        (B) TYPE: nucleic acid
        (C) STRANDEDNESS: unknown
        (D) TOPOLOGY: unknown (ii) MOLECULE TYPE: cDNA (ix) FEATURE:
         (A) NAME/KEY: misc_feature
         (B) LOCATION: 1..31
         (D) OTHER INFORMATION: /note= "Bovine P-450 (rev)"

(xi) SEQUENCE DESCRIPTION: SEQ ID NO:33:

AGTTCTTCAG GACCNTGGAG AGNGGCAGGG T                                        31

(2) INFORMATION FOR SEQ ID NO:34:

(i) SEQUENCE CHARACTERISTICS:
        (A) LENGTH: 31 base pairs
        (B) TYPE: nucleic acid
        (C) STRANDEDNESS: unknown
        (D) TOPOLOGY: unknown (ii) MOLECULE TYPE: cDNA (ix) FEATURE:
         (A) NAME/KEY: misc_feature
         (B) LOCATION: 1..31
         (D) OTHER INFORMATION: /note= "Canine Distemper Virus (rev)"

(xi) SEQUENCE DESCRIPTION: SEQ ID NO:34:

TGTCTTTCCG TACCNCGGAG AGNGCCAGAG T                                        31

(2) INFORMATION FOR SEQ ID NO:35:

(i) SEQUENCE CHARACTERISTICS:
        (A) LENGTH: 31 base pairs
        (B) TYPE: nucleic acid
        (C) STRANDEDNESS: unknown
        (D) TOPOLOGY: unknown (ii) MOLECULE TYPE: cDNA (ix) FEATURE:
         (A) NAME/KEY: misc_feature
         (B) LOCATION: 1..31
         (D) OTHER INFORMATION: /note= "Sheep Keratin"

(xi) SEQUENCE DESCRIPTION: SEQ ID NO:35:

ATGTGATCAG CACCNCGGAG AGNGGCATGA G                                        31

(2) INFORMATION FOR SEQ ID NO:36:

(i) SEQUENCE CHARACTERISTICS:
        (A) LENGTH: 31 base pairs
        (B) TYPE: nucleic acid
        (C) STRANDEDNESS: unknown
        (D) TOPOLOGY: unknown (ii) MOLECULE TYPE: cDNA (ix) FEATURE:
    (A) NAME/KEY: misc_feature
    (B) LOCATION: 1..31
    (D) OTHER INFORMATION: /note= "Mouse Skeletal Actin (rev)"

(xi) SEQUENCE DESCRIPTION: SEQ ID NO:36:

GCTTCGGCAG CACCNCGGCG AGNGCCGCCA G                          31

(2) INFORMATION FOR SEQ ID NO:37:

(i) SEQUENCE CHARACTERISTICS:
        (A) LENGTH: 31 base pairs
        (B) TYPE: nucleic acid
        (C) STRANDEDNESS: unknown
        (D) TOPOLOGY: unknown (ii) MOLECULE TYPE: cDNA (ix) FEATURE:
        (A) NAME/KEY: misc_feature
        (B) LOCATION: 1..31
        (D) OTHER INFORMATION: /note= "T-Cell Receptor Beta"

(xi) SEQUENCE DESCRIPTION: SEQ ID NO:37:

GTACCGTCAG CAACNTGGAG AGNGCCTGAC A                          31

(2) INFORMATION FOR SEQ ID NO:38:

(i) SEQUENCE CHARACTERISTICS:
        (A) LENGTH: 31 base pairs
        (B) TYPE: nucleic acid
        (C) STRANDEDNESS: unknown
        (D) TOPOLOGY: unknown (ii) MOLECULE TYPE: cDNA (ix) FEATURE:
        (A) NAME/KEY: misc_feature
        (B) LOCATION: 1..31
        (D) OTHER INFORMATION: /note= "Pig Lactalbumin (rev)"

(xi) SEQUENCE DESCRIPTION: SEQ ID NO:38:

TGTCTTTCAG CACCNGGGAG AGNTCACATT T                          31

(2) INFORMATION FOR SEQ ID NO:39:

(i) SEQUENCE CHARACTERISTICS:
        (A) LENGTH: 2043 base pairs
        (B) TYPE: nucleic acid
        (C) STRANDEDNESS: unknown
        (D) TOPOLOGY: unknown (ii) MOLECULE TYPE: cDNA (ix) FEATURE:
        (A) NAME/KEY: CDS
        (B) LOCATION: 8..2035

(xi) SEQUENCE DESCRIPTION: SEQ ID NO:39:

```
GAATTCC GGG GCC CCA GAC CCT GGC GGC GGC TGC GGC AGC CGA GAC GGC        49
        Gly Ala Pro Asp Pro Gly Gly Gly Cys Gly Ser Arg Asp Gly
         1               5                  10

AGG GCG AGG CCC GGA GGC CTG AGC ACC CTC TGC AGC CCC ACT CCT GGG        97
Arg Ala Arg Pro Gly Gly Leu Ser Thr Leu Cys Ser Pro Thr Pro Gly
 15              20                  25                  30

CCT TCT TGG TCC ACG ACG GCC CCA GCA CCC AAC TTT ACC ACC CTC CCC       145
Pro Ser Trp Ser Thr Thr Ala Pro Ala Pro Asn Phe Thr Thr Leu Pro
             35                  40                  45
```

```
CAC CTC TCC CCC GAA ACT CCA GCA ACA AAG AAA AGT AGT CGG AGA AGG    193
His Leu Ser Pro Glu Thr Pro Ala Thr Lys Lys Ser Ser Arg Arg Arg
            50                  55                  60

AGC GGC GAC TCA GGG TCG CCC GCC CCT CCT CAC CGA GGA AGG CCG AAT    241
Ser Gly Asp Ser Gly Ser Pro Ala Pro Pro His Arg Gly Arg Pro Asn
            65                  70                  75

ACA GTT ATG GCC ACC CAG GTA ATG GGG CAG TCT TCT GGA GGA GGA GGG    289
Thr Val Met Ala Thr Gln Val Met Gly Gln Ser Ser Gly Gly Gly Gly
        80                  85                  90

CTG TTT ACC AGC AGT GGC AAC ATT GGA ATG GCC CTG CCT AAC GAC ATG    337
Leu Phe Thr Ser Ser Gly Asn Ile Gly Met Ala Leu Pro Asn Asp Met
95                  100                 105                 110

TAT GAC TTG CAT GAC CTT TCC AAA GCT GAA CTG GCC GCA CCT CAG CTT    385
Tyr Asp Leu His Asp Leu Ser Lys Ala Glu Leu Ala Ala Pro Gln Leu
                115                 120                 125

ATT ATG CTG GCA AAT GTG GCC TTA ACT GGG GAA GTA AAT GGC AGC TGC    433
Ile Met Leu Ala Asn Val Ala Leu Thr Gly Glu Val Asn Gly Ser Cys
            130                 135                 140

TGT GAT TAC CTG GTC GGT GAA GAA AGA CAG ATG GCA GAA CTG ATG CCG    481
Cys Asp Tyr Leu Val Gly Glu Glu Arg Gln Met Ala Glu Leu Met Pro
            145                 150                 155

GTT GGG GAT AAC AAC TTT TCA GAT AGT GAA GAA GGA GAA GGA CTT GAA    529
Val Gly Asp Asn Asn Phe Ser Asp Ser Glu Glu Gly Glu Gly Leu Glu
        160                 165                 170

GAG TCT GCT GAT ATA AAA GGT GAA CCT CAT GGA CTG GAA AAC ATG GAA    577
Glu Ser Ala Asp Ile Lys Gly Glu Pro His Gly Leu Glu Asn Met Glu
175                 180                 185                 190

CTG AGA AGT TTG GAA CTC AGC GTC GTA GAA CCT CAG CCT GTA TTT GAG    625
Leu Arg Ser Leu Glu Leu Ser Val Val Glu Pro Gln Pro Val Phe Glu
                195                 200                 205

GCA TCA GGT GCT CCA GAT ATT TAC AGT TCA AAT AAA GAT CTT CCC CCT    673
Ala Ser Gly Ala Pro Asp Ile Tyr Ser Ser Asn Lys Asp Leu Pro Pro
            210                 215                 220

GAA ACA CCT GGA GCG GAG GAC AAA GGC AAG AGC TCG AAG ACC AAA CCC    721
Glu Thr Pro Gly Ala Glu Asp Lys Gly Lys Ser Ser Lys Thr Lys Pro
            225                 230                 235

TTT CGC TGT AAG CCA TGC CAA TAT GAA GCA GAA TCT GAA GAA CAG TTT    769
Phe Arg Cys Lys Pro Cys Gln Tyr Glu Ala Glu Ser Glu Glu Gln Phe
        240                 245                 250

GTG CAT CAC ATC AGA GTT CAC AGT GCT AAG AAA TTT TTT GTG GAA GAG    817
Val His His Ile Arg Val His Ser Ala Lys Lys Phe Phe Val Glu Glu
255                 260                 265                 270

AGT GCA GAG AAG CAG GCA AAA GCC AGG GAA TCT GGC TCT TCC ACT GCA    865
Ser Ala Glu Lys Gln Ala Lys Ala Arg Glu Ser Gly Ser Ser Thr Ala
                275                 280                 285

GAA GAG GGA GAT TTC TCC AAG GGC CCC ATT CGC TGT GAC CGC TGC GGC    913
Glu Glu Gly Asp Phe Ser Lys Gly Pro Ile Arg Cys Asp Arg Cys Gly
            290                 295                 300

TAC AAT ACT AAT CGA TAT GAT CAC TAT ACA GCA CAC CTG AAA CAC CAC    961
Tyr Asn Thr Asn Arg Tyr Asp His Tyr Thr Ala His Leu Lys His His
            305                 310                 315

ACC AGA GCT GGG GAT AAT GAG CGA GTC TAC AAG TGT ATC ATT TGC ACA    1009
Thr Arg Ala Gly Asp Asn Glu Arg Val Tyr Lys Cys Ile Ile Cys Thr
        320                 325                 330

TAC ACA ACA GTG AGC GAG TAT CAC TGG AGG AAA CAT TTA AGA AAC CAT    1057
Tyr Thr Thr Val Ser Glu Tyr His Trp Arg Lys His Leu Arg Asn His
335                 340                 345                 350

TTT CCA AGG AAA GTA TAC ACA TGT GGA AAA TGC AAC TAT TTT TCA GAC    1105
Phe Pro Arg Lys Val Tyr Thr Cys Gly Lys Cys Asn Tyr Phe Ser Asp
                355                 360                 365
```

```
AGA AAA AAC AAT TAT GTT CAG CAT GTT AGA ACT CAT ACA GGA GAA CGC      1153
Arg Lys Asn Asn Tyr Val Gln His Val Arg Thr His Thr Gly Glu Arg
            370                 375                 380

CCA TAT AAA TGT GAA CTT TGT CCT TAC TCA AGT TCT CAG AAG ACT CAT      1201
Pro Tyr Lys Cys Glu Leu Cys Pro Tyr Ser Ser Ser Gln Lys Thr His
        385                 390                 395

CTA ACT AGA CAT ATG CGT ACT CAT TCA GGT GAG AAG CCA TTT AAA TGT      1249
Leu Thr Arg His Met Arg Thr His Ser Gly Glu Lys Pro Phe Lys Cys
400                 405                 410

GAT CAG TGC AGT TAT GTG GCC TCT AAT CAA CAT GAA GTA ACC CGC CAT      1297
Asp Gln Cys Ser Tyr Val Ala Ser Asn Gln His Glu Val Thr Arg His
415                 420                 425                 430

GCA AGA CAG GTT CAC AAT GGG CCT AAA CCT CTT AAT TGC CCA CAC TGT      1345
Ala Arg Gln Val His Asn Gly Pro Lys Pro Leu Asn Cys Pro His Cys
                435                 440                 445

GAT TAC AAA ACA GCA GAT AGA AGC AAC TTC AAA AAA CAT GTA GAG CTA      1393
Asp Tyr Lys Thr Ala Asp Arg Ser Asn Phe Lys Lys His Val Glu Leu
            450                 455                 460

CAT GTG AAC CCA CGG CAG TTC AAT TGC CCT GTA TGT GAC TAT GCA GCT      1441
His Val Asn Pro Arg Gln Phe Asn Cys Pro Val Cys Asp Tyr Ala Ala
        465                 470                 475

TCC AAG AAG TGT AAT CTA CAG TAT CAC TTC AAA TCT AAG CAT CCT ACT      1489
Ser Lys Lys Cys Asn Leu Gln Tyr His Phe Lys Ser Lys His Pro Thr
    480                 485                 490

TGT CCT AAT AAA ACA ATG GAT GTC TCA AAA GTG AAA CTA AAG AAA ACC      1537
Cys Pro Asn Lys Thr Met Asp Val Ser Lys Val Lys Leu Lys Lys Thr
495                 500                 505                 510

AAA AAA CGA GAG GCT GAC TTG CCT GAT AAT ATT ACC AAT GAA AAA ACA      1585
Lys Lys Arg Glu Ala Asp Leu Pro Asp Asn Ile Thr Asn Glu Lys Thr
                515                 520                 525

GAA ATA GAA CAA ACA AAA ATA AAA GGG GAT GTG GCT GGA AAG AAA AAT      1633
Glu Ile Glu Gln Thr Lys Ile Lys Gly Asp Val Ala Gly Lys Lys Asn
            530                 535                 540

GAA AAG TCC GTC AAA GCA GAG AAA AGA GAT GTC TCA AAA GAG AAA AAG      1681
Glu Lys Ser Val Lys Ala Glu Lys Arg Asp Val Ser Lys Glu Lys Lys
        545                 550                 555

CCT TCT AAT AAT GTG TCA GTG ATC CAG GTG ACT ACC AGA ACT CGA AAA      1729
Pro Ser Asn Asn Val Ser Val Ile Gln Val Thr Thr Arg Thr Arg Lys
    560                 565                 570

TCA GTA ACA GAG GTG AAA GAG ATG GAT GTG CAT ACA GGA AGC AAT TCA      1777
Ser Val Thr Glu Val Lys Glu Met Asp Val His Thr Gly Ser Asn Ser
575                 580                 585                 590

GAA AAA TTC AGT AAA ACT AAG AAA AGC AAA AGG AAG CTG GAA GTT GAC      1825
Glu Lys Phe Ser Lys Thr Lys Lys Ser Lys Arg Lys Leu Glu Val Asp
                595                 600                 605

AGC CAT TCT TTA CAT GGT CCT GTG AAT GAT GAG GAA TCT TCA ACA AAA      1873
Ser His Ser Leu His Gly Pro Val Asn Asp Glu Glu Ser Ser Thr Lys
            610                 615                 620

AAG AAA AAG AAG GTA GAA AGC AAA TCC AAA AAT AAT AGT CAG GAA GTG      1921
Lys Lys Lys Lys Val Glu Ser Lys Ser Lys Asn Asn Ser Gln Glu Val
        625                 630                 635

CCA AAG GGT GAC AGC AAA GTG GAG GAG AAT AAA AAG CAA AAT ACT TGC      1969
Pro Lys Gly Asp Ser Lys Val Glu Glu Asn Lys Lys Gln Asn Thr Cys
    640                 645                 650

ATG AAA AAA AGT ACA AAG AAG AAA ACT CTG AAA AAT AAA TCA AGT AAG      2017
Met Lys Lys Ser Thr Lys Lys Lys Thr Leu Lys Asn Lys Ser Ser Lys
655                 660                 665                 670

AAA AGC AGT AAG CCT TCT CGGAATTC                                     2043
Lys Ser Ser Lys Pro Ser
                675
```

(2) INFORMATION FOR SEQ ID NO:40:

(i) SEQUENCE CHARACTERISTICS:
        (A) LENGTH: 676 amino acids
        (B) TYPE: amino acid
        (D) TOPOLOGY: linear (ii) MOLECULE TYPE: protein (xi) SEQUENCE DESCRIPTION: SEQ ID NO:40:

```
Gly Ala Pro Asp Pro Gly Gly Cys Gly Ser Arg Asp Gly Arg Ala
 1               5                  10                  15

Arg Pro Gly Gly Leu Ser Thr Leu Cys Ser Pro Thr Pro Gly Pro Ser
                 20                  25                  30

Trp Ser Thr Thr Ala Pro Ala Pro Asn Phe Thr Thr Leu Pro His Leu
                 35                  40                  45

Ser Pro Glu Thr Pro Ala Thr Lys Lys Ser Ser Arg Arg Arg Ser Gly
 50                  55                  60

Asp Ser Gly Ser Pro Ala Pro Pro His Arg Gly Arg Pro Asn Thr Val
 65                  70                  75                  80

Met Ala Thr Gln Val Met Gly Gln Ser Ser Gly Gly Gly Leu Phe
                 85                  90                  95

Thr Ser Ser Gly Asn Ile Gly Met Ala Leu Pro Asn Asp Met Tyr Asp
                 100                 105                 110

Leu His Asp Leu Ser Lys Ala Glu Leu Ala Ala Pro Gln Leu Ile Met
                 115                 120                 125

Leu Ala Asn Val Ala Leu Thr Gly Glu Val Asn Gly Ser Cys Cys Asp
 130                 135                 140

Tyr Leu Val Gly Glu Glu Arg Gln Met Ala Glu Leu Met Pro Val Gly
 145                 150                 155                 160

Asp Asn Asn Phe Ser Asp Ser Glu Glu Gly Gly Leu Glu Glu Ser
                 165                 170                 175

Ala Asp Ile Lys Gly Glu Pro His Gly Leu Glu Asn Met Glu Leu Arg
                 180                 185                 190

Ser Leu Glu Leu Ser Val Val Glu Pro Gln Pro Val Phe Glu Ala Ser
                 195                 200                 205

Gly Ala Pro Asp Ile Tyr Ser Ser Asn Lys Asp Leu Pro Pro Glu Thr
 210                 215                 220

Pro Gly Ala Glu Asp Lys Gly Lys Ser Ser Lys Thr Lys Pro Phe Arg
225                  230                 235                 240

Cys Lys Pro Cys Gln Tyr Glu Ala Glu Ser Glu Glu Gln Phe Val His
                 245                 250                 255

His Ile Arg Val His Ser Ala Lys Lys Phe Phe Val Glu Glu Ser Ala
                 260                 265                 270

Glu Lys Gln Ala Lys Ala Arg Glu Ser Gly Ser Ser Thr Ala Glu Glu
                 275                 280                 285

Gly Asp Phe Ser Lys Gly Pro Ile Arg Cys Asp Arg Cys Gly Tyr Asn
                 290                 295                 300

Thr Asn Arg Tyr Asp His Tyr Thr Ala His Leu Lys His His Thr Arg
305                  310                 315                 320

Ala Gly Asp Asn Glu Arg Val Tyr Lys Cys Ile Ile Cys Thr Tyr Thr
                 325                 330                 335

Thr Val Ser Glu Tyr His Trp Arg Lys His Leu Arg Asn His Phe Pro
                 340                 345                 350

Arg Lys Val Tyr Thr Cys Gly Lys Cys Asn Tyr Phe Ser Asp Arg Lys
```

```
                355                 360                 365
Asn Asn Tyr Val Gln His Val Arg Thr His Thr Gly Glu Arg Pro Tyr
    370                 375                 380
Lys Cys Glu Leu Cys Pro Tyr Ser Ser Gln Lys Thr His Leu Thr
385                 390                 395                 400
Arg His Met Arg Thr His Ser Gly Glu Lys Pro Phe Lys Cys Asp Gln
                405                 410                 415
Cys Ser Tyr Val Ala Ser Asn Gln His Glu Val Thr Arg His Ala Arg
                420                 425                 430
Gln Val His Asn Gly Pro Lys Pro Leu Asn Cys Pro His Cys Asp Tyr
            435                 440                 445
Lys Thr Ala Asp Arg Ser Asn Phe Lys Lys His Val Glu Leu His Val
450                 455                 460
Asn Pro Arg Gln Phe Asn Cys Pro Val Cys Asp Tyr Ala Ala Ser Lys
465                 470                 475                 480
Lys Cys Asn Leu Gln Tyr His Phe Lys Ser Lys His Pro Thr Cys Pro
                485                 490                 495
Asn Lys Thr Met Asp Val Ser Lys Val Lys Leu Lys Thr Lys Lys
                500                 505                 510
Arg Glu Ala Asp Leu Pro Asp Asn Ile Thr Asn Glu Lys Thr Glu Ile
                515                 520                 525
Glu Gln Thr Lys Ile Lys Gly Asp Val Ala Gly Lys Lys Asn Glu Lys
                530                 535                 540
Ser Val Lys Ala Glu Lys Arg Asp Val Ser Lys Glu Lys Pro Ser
545                 550                 555                 560
Asn Asn Val Ser Val Ile Gln Val Thr Thr Arg Thr Arg Lys Ser Val
                565                 570                 575
Thr Glu Val Lys Glu Met Asp Val His Thr Gly Ser Asn Ser Glu Lys
                580                 585                 590
Phe Ser Lys Thr Lys Ser Lys Arg Lys Leu Glu Val Asp Ser His
            595                 600                 605
Ser Leu His Gly Pro Val Asn Asp Glu Glu Ser Ser Thr Lys Lys
            610                 615                 620
Lys Lys Val Glu Ser Lys Ser Lys Asn Asn Ser Gln Glu Val Pro Lys
625                 630                 635                 640
Gly Asp Ser Lys Val Glu Glu Asn Lys Lys Gln Asn Thr Cys Met Lys
                645                 650                 655
Lys Ser Thr Lys Lys Thr Leu Lys Asn Lys Ser Ser Lys Lys Ser
            660                 665                 670
Ser Lys Pro Ser
        675

(2) INFORMATION FOR SEQ ID NO:41:

(i) SEQUENCE CHARACTERISTICS:
        (A) LENGTH: 23 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:41:

Phe Arg Cys Lys Pro Cys Gln Tyr Glu Ala Glu Ser Glu Glu Gln Phe
1               5                   10                  15

Val His His Ile Arg Val His
                20
```

(2) INFORMATION FOR SEQ ID NO:42:

(i) SEQUENCE CHARACTERISTICS:
        (A) LENGTH: 32 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:42:

```
Ile Arg Cys Asp Arg Cys Gly Tyr Asn Thr Asn Arg Tyr Asp His Tyr
1               5                   10                  15
Thr Ala His Leu Lys His His Thr Arg Ala Gly Asp Asn Glu Arg Val
            20                  25                  30
```

(2) INFORMATION FOR SEQ ID NO:43:

(i) SEQUENCE CHARACTERISTICS:
        (A) LENGTH: 28 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:43:

```
Tyr Lys Cys Ile Ile Cys Thr Tyr Thr Thr Val Ser Glu Tyr His Trp
1               5                   10                  15
Arg Lys His Leu Arg Asn His Phe Pro Arg Lys Val
            20                  25
```

(2) INFORMATION FOR SEQ ID NO:44:

(i) SEQUENCE CHARACTERISTICS:
        (A) LENGTH: 28 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:44:

```
Tyr Thr Cys Gly Lys Cys Asn Tyr Phe Ser Asp Arg Lys Asn Asn Tyr
1               5                   10                  15
Val Gln His Val Arg Thr His Thr Gly Glu Arg Pro
            20                  25
```

(2) INFORMATION FOR SEQ ID NO:45:

(i) SEQUENCE CHARACTERISTICS:
        (A) LENGTH: 28 amino acids
        (B) TYPE: amino acid
        (C) STRANDEDNESS: unknown
        (D) TOPOLOGY: unknown (ii) MOLECULE TYPE: protein (xi) SEQUENCE DESCRIPTION: SEQ ID NO:45:

```
Tyr Lys Cys Glu Leu Cys Pro Tyr Ser Ser Gln Lys Thr His Leu
1               5                   10                  15
Thr Arg His Met Arg Thr His Ser Gly Glu Lys Pro
            20                  25
```

(2) INFORMATION FOR SEQ ID NO:46:

(i) SEQUENCE CHARACTERISTICS:
              (A) LENGTH: 29 amino acids
              (B) TYPE: amino acid
              (C) STRANDEDNESS: unknown
              (D) TOPOLOGY: unknown (ii) MOLECULE TYPE: protein (xi) SEQUENCE DESCRIPTION: SEQ ID NO:46:

Phe Lys Cys Asp Gln Cys Ser Tyr Val Ala Ser Asn Gln His Glu Val
1               5                   10                  15

Thr Arg His Ala Arg Gln Val His Asn Gly Pro Lys Pro
            20                  25

(2) INFORMATION FOR SEQ ID NO:47:

(i) SEQUENCE CHARACTERISTICS:
              (A) LENGTH: 28 amino acids
              (B) TYPE: amino acid
              (C) STRANDEDNESS: unknown
              (D) TOPOLOGY: unknown (ii) MOLECULE TYPE: protein (xi) SEQUENCE DESCRIPTION: SEQ ID NO:47:

Leu Asn Cys Pro His Cys Asp Tyr Lys Thr Ala Asp Arg Ser Asn Phe
1               5                   10                  15

Lys Lys His Val Glu Leu His Val Asn Pro Arg Gln
            20                  25

(2) INFORMATION FOR SEQ ID NO:48:

(i) SEQUENCE CHARACTERISTICS:
              (A) LENGTH: 24 amino acids
              (B) TYPE: amino acid
              (C) STRANDEDNESS: unknown
              (D) TOPOLOGY: unknown (ii) MOLECULE TYPE: protein (xi) SEQUENCE DESCRIPTION: SEQ ID NO:48:

Phe Asn Cys Pro Val Cys Asp Tyr Ala Ala Ser Lys Lys Cys Asn Leu
1               5                   10                  15

Gln Tyr His Phe Lys Ser Lys His
            20

(2) INFORMATION FOR SEQ ID NO:49:

(i) SEQUENCE CHARACTERISTICS:
              (A) LENGTH: 40 base pairs
              (B) TYPE: nucleic acid
              (C) STRANDEDNESS: unknown
              (D) TOPOLOGY: unknown (ii) MOLECULE TYPE: DNA (genomic)

(xi) SEQUENCE DESCRIPTION: SEQ ID NO:49:

AGCTGCAAAG CCATTTCAGC ACCACGGAGA GTGCCTCTGC                          40

(2) INFORMATION FOR SEQ ID NO:50:

(i) SEQUENCE CHARACTERISTICS:
              (A) LENGTH: 37 base pairs
              (B) TYPE: nucleic acid
              (C) STRANDEDNESS: unknown
              (D) TOPOLOGY: unknown (ii) MOLECULE TYPE: DNA (genomic)

```
    (ix) FEATURE:
        (A) NAME/KEY: misc_feature
        (B) LOCATION: 3..4
        (D) OTHER INFORMATION: /note= "Let 'N' at position 3
            represent 'e'."

(xi) SEQUENCE DESCRIPTION: SEQ ID NO:50:

AGNATTGGGT TTCAGAACCA CGGACAGCAC CAGAGTA                    37

(2) INFORMATION FOR SEQ ID NO:51:

(i) SEQUENCE CHARACTERISTICS:
        (A) LENGTH: 39 base pairs
        (B) TYPE: nucleic acid
        (C) STRANDEDNESS: unknown
        (D) TOPOLOGY: unknown (ii) MOLECULE TYPE: DNA (genomic)

(ix) FEATURE:
        (A) NAME/KEY: misc_feature
        (B) LOCATION: 3..4
        (D) OTHER INFORMATION: /note= "Let 'N' at position 3
            represent 'e'."

(xi) SEQUENCE DESCRIPTION: SEQ ID NO:51:

AGNTTATGCC AGCTTCAGCA CCGCGGACAG TGCCTTCCA                  39

(2) INFORMATION FOR SEQ ID NO:52:

(i) SEQUENCE CHARACTERISTICS:
        (A) LENGTH: 40 base pairs
        (B) TYPE: nucleic acid
        (C) STRANDEDNESS: unknown
        (D) TOPOLOGY: unknown (ii) MOLECULE TYPE: DNA (genomic)

(ix) FEATURE:
        (A) NAME/KEY: misc_feature
        (B) LOCATION: 3..4
        (D) OTHER INFORMATION: /note= "Let 'N' at position 3
            represent 'e'."

(xi) SEQUENCE DESCRIPTION: SEQ ID NO:52:

AGNTTAGAGT CCATTCAGCA CCTTGGACAG AGCCAGCGGA                 40

(2) INFORMATION FOR SEQ ID NO:53:

(i) SEQUENCE CHARACTERISTICS:
        (A) LENGTH: 27 base pairs
        (B) TYPE: nucleic acid
        (C) STRANDEDNESS: unknown
        (D) TOPOLOGY: unknown (ii) MOLECULE TYPE: DNA (genomic)

(ix) FEATURE:
        (A) NAME/KEY: misc_feature
        (B) LOCATION: 3..4
        (D) OTHER INFORMATION: /note= "Let 'N' at position 3
            represent 'e'."

(xi) SEQUENCE DESCRIPTION: SEQ ID NO:53:

AGNTTGCGGA ACGGAAGCGG AAACCGA                               27
```